US010690661B2

(12) United States Patent
Tyo et al.

(10) Patent No.: US 10,690,661 B2
(45) Date of Patent: Jun. 23, 2020

(54) YEAST-BASED BIOSENSOR

(71) Applicant: Northwestern University, Evanston, IL (US)

(72) Inventors: Keith E. J. Tyo, Evanston, IL (US); Adebola V. Adeniran, Evanston, IL (US); John W. Bostick, Evanston, IL (US); Dante A. Pertusi, Evanston, IL (US); Sarah Christine Stainbrook, Evanston, IL (US)

(73) Assignee: Northwestern University, Evanston, IL (US)

( * ) Notice: Subject to any disclaimer, the term of this patent is extended or adjusted under 35 U.S.C. 154(b) by 13 days.

(21) Appl. No.: 15/324,986

(22) PCT Filed: Jul. 10, 2015

(86) PCT No.: PCT/US2015/039996
§ 371 (c)(1),
(2) Date: Jan. 9, 2017

(87) PCT Pub. No.: WO2016/007886
PCT Pub. Date: Jan. 14, 2016

(65) Prior Publication Data
US 2017/0205401 A1    Jul. 20, 2017

Related U.S. Application Data

(60) Provisional application No. 62/023,549, filed on Jul. 11, 2014.

(51) Int. Cl.
*G01N 33/542* (2006.01)
*C07K 14/395* (2006.01)

(52) U.S. Cl.
CPC ......... *G01N 33/542* (2013.01); *C07K 14/395* (2013.01); *G01N 2333/395* (2013.01)

(58) Field of Classification Search
None
See application file for complete search history.

(56) References Cited

U.S. PATENT DOCUMENTS

| | | | |
|---|---|---|---|
| 5,625,048 A | 4/1997 | Tsien et al. | |
| 5,777,079 A | 7/1998 | Tsien et al. | |
| 5,804,387 A | 9/1998 | Cormack et al. | |
| 5,821,063 A | 10/1998 | Patterson et al. | |
| 5,874,304 A | 2/1999 | Zolotukhin et al. | |
| 5,968,750 A | 10/1999 | Zolotukhin et al. | |
| 6,020,192 A | 2/2000 | Muzyczka et al. | |
| 6,054,321 A | 4/2000 | Tsien et al. | |
| 6,090,919 A | 7/2000 | Cormack et al. | |
| 6,096,865 A | 8/2000 | Michaels | |
| 6,146,826 A | 11/2000 | Chalfie et al. | |
| 7,544,477 B2 * | 6/2009 | Balint ............... | C07K 16/00 424/134.1 |
| 7,604,592 B2 | 10/2009 | Freeman et al. | |
| 8,005,686 B2 | 8/2011 | Smith | |
| 8,110,392 B2 | 2/2012 | Dicosimo et al. | |
| 8,283,155 B2 | 10/2012 | Holmes et al. | |
| 8,523,797 B2 | 9/2013 | Lowery et al. | |
| 8,647,887 B2 * | 2/2014 | Trowell ............... | G01N 33/542 435/69.7 |
| 8,697,377 B2 | 4/2014 | Burd et al. | |
| 9,809,862 B2 * | 11/2017 | Peralta-Yahya ...... | C12Q 1/6897 |
| 2005/0054050 A1 | 3/2005 | Thastrup et al. | |
| 2007/0105184 A1 | 5/2007 | Greenbaum et al. | |
| 2008/0070794 A1 | 3/2008 | Broach et al. | |
| 2010/0261178 A1 | 10/2010 | Lyons et al. | |
| 2012/0077210 A1 * | 3/2012 | Trowell ............... | G01N 33/542 435/7.9 |
| 2013/0210652 A1 | 8/2013 | Chakravarthy et al. | |
| 2014/0234851 A1 | 8/2014 | Leonard et al. | |
| 2014/0320807 A1 | 10/2014 | Thangaraju et al. | |

(Continued)

FOREIGN PATENT DOCUMENTS

EP              1248840 A2 * 10/2002 ............. C07K 16/00
WO    WO 1997/035985        10/1997

(Continued)

OTHER PUBLICATIONS

Adeniran, Adebola; Stainbrook, Sarah; Bostick, John; Tyo, Keith Source: ACS Synthetic Biology (2018) Ahead of Print. abstract only (Year: 2018).*
Adeniran et al, FEMS Yeast Research, 2015, 15:1-15, (Year: 2015).*
Adeniran, Adebola; Stainbrook, Sarah; Tyo, Keith, 2016, Chemical Biological Engineering, Abstracts of Papers, 251st ACS National Meeting & Exposition, abstract only (Year: 2016).*
Liu et al, Biotechnol. Bioeng. 2012;109: 1259-1268. published online Dec. 16, 2011 (Year: 2012).*
Stainbrook et al, Protein Engineering, Design & Selection, 2017, vol. 30 No. 6, pp. 455-465. Advanced Access Publication Date: Apr. 27, 2017 (Year: 2017).*

(Continued)

*Primary Examiner* — Nita M. Minnifield
(74) *Attorney, Agent, or Firm* — Foley & Lardner LLP

(57) ABSTRACT

Provided herein are compositions and systems comprising yeast-based biosensors (YBBs) and methods of use thereof. In particular, YBBs are provided for the detection and/or quantification of an analyte (e.g., peptide analyte) in a sample (e.g., a biological sample, environmental sample, etc.). In some embodiments, provided herein are diagnostic compositions, devices, and methods comprising yeast-based biosensors (YBBs) engineered to detect analytes (e.g., peptides (e.g., biomarker peptides, etc.), etc.). In some embodiments, YBBs comprise (a) recognition element (e.g., receptor (e.g., modified yeast receptor, etc.), etc.) on the exterior of the biosensor (e.g., for binding and or recognition of the analyte (e.g., peptide)), and (b) a reporter that signals binding or recognition of the analyte. In some embodiments, a recognition element is a cell surface receptor.

20 Claims, 18 Drawing Sheets

Specification includes a Sequence Listing.

(56) References Cited

U.S. PATENT DOCUMENTS

| | | | |
|---|---|---|---|
| 2016/0122832 A1* | 5/2016 | Peralta-Yahya | C12Q 1/6897 435/6.1 |
| 2016/0202761 A1* | 7/2016 | Bostick | G06F 3/016 345/174 |
| 2017/0205401 A1* | 7/2017 | Tyo | G01N 33/542 |

FOREIGN PATENT DOCUMENTS

| | | | | |
|---|---|---|---|---|
| WO | WO 2002/046369 | | 6/2002 | |
| WO | WO-2009093118 A1 * | | 7/2009 | C07K 14/33 |
| WO | WO 2013/022739 | | 2/2013 | |
| WO | WO 2014/134537 | | 9/2014 | |
| WO | WO-2014188335 A1 * | | 11/2014 | C12N 15/81 |
| WO | WO 2016/007886 | | 1/2016 | |
| WO | WO-2016007886 A1 * | | 1/2016 | C07K 14/395 |

OTHER PUBLICATIONS

Han et al, Appl. Biochem. Biotechnol., 2017, 23 pages. published online: Nov. 22, 2017 (Year: 2017).*
Abel et al., Mutations affecting ligand specificity of the G-protein-coupled receptor for the *Saccharomyces cerevisiae* tridecapeptide pheromone. Biochim Biophys Acta. 1998;1448(1):12-26.
Aluise et al., Peptides and proteins in plasma and cerebrospinal fluid as biomarkers for the prediction, diagnosis, and monitoring of therapeutic efficacy of Alzheimer's disease. Biochim Biophys Acta. 2008;1782(10):549-58.
Armbruster et al., Evolving the lock to fit the key to create a family of G protein-coupled receptors potently activated by an inert ligand. Proceedings of the National Academy of Sciences of the United States of America. 2007;104(12):5163-8.
Ault et al., Creation of GPCR-based chemical sensors by directed evolution in yeast. Protein Eng Des Sel. Jan. 2006;19(1):1-8.
Chepurny et al., A novel cyclic adenosine monophosphate responsive luciferase reporter incorporating a nonpalindromic cyclic adenosine monophosphate response element provides optimal performance for use in G protein coupled receptor drug discovery efforts. J Biomol Screen. Aug. 2007;12(5):740-6.
Coresh et al., Prevalence of chronic kidney disease in the United States. JAMA. Nov. 7, 2007;298(17):2038-47.
Coward et al., Controlling signaling with a specifically designed Gi-coupled receptor. Proc Natl Acad Sci U S A. Jan. 6, 1998;95(1):352-7.
Dharnidharka et al., Serum cystatin C is superior to serum creatinine as a marker of kidney function: a meta-analysis. Am J Kidney Dis. Aug. 2002;40(2):221-6.
Herskowitz, MAP kinase pathways in yeast: for mating and more. Cell. 1995;80(2):187-97.
Keppler-Ross et al., A new purple fluorescent color marker for genetic studies in *Saccharomyces cerevisiae* and Candida albicans. Genetics. 2008;179(1):705-10.
Kobilka et al., New G-protein-coupled receptor crystal structures: insights and limitations. Trends Pharmacol Sci. Feb. 2008;29(2):79-83.
Lewis et al., Improved immunoturbidimetric assay for cystatin C. Ann Clin Biochem. Mar. 2001;38(Pt 2):111-4.
Lifetechnologies. TrypLE™ Express Enzyme (1X), no phenol red accessed 2014. tools.lifetechnologies.com/content/sfs/manuals/trypIE_man.pdf. 2 pages.
Mathew et al., Differential Interactions of Fluorescent Agonists and Antagonists with the Yeast G Protein Coupled Receptor Ste2p. J Mol Biol. 2011;409:513-28.
McCusker et al., Heterologous GPCR expression: A bottleneck to obtaining crystal structures. Biotechnol Prog. May-Jun. 2007;23(3):540-7.
McDonnell et al., Cardiac biomarkers and the case for point-of-care testing. Clin Biochem. May 2009;42(7-8):549-61.
Naider et al., The alpha-factor mating pheromone of *Saccharomyces cerevisiae*: a model for studying the interaction of peptide hormones and G protein-coupled receptors. Peptides. Sep. 2004;25(9):1441-63.
Petricoin et al., The blood peptidome: a higher dimension of information content for cancer biomarker discovery. Nat Rev Cancer. Dec. 2006;6(12):961-7.
Randers et al., Serum cystatin C as an endogenous parameter of the renal function in patients with normal to moderately impaired kidney function. Clin Nephrol. Sep. 2000;54(3):203-9.
Romero et al., Exploring protein fitness landscapes by directed evolution. Nat Rev Mol Cell Biol. Dec. 2009;10(12):866-76.
Rosenbaum et al., The structure and function of G-protein-coupled receptors. Nature. May 21, 2009;459(7245):356-63.
Schaberg et al., Risk factors for side-effects of isoniazid, rifampin and pyrazinamide in patients hospitalized for pulmonary tuberculosis. Eur Respir J. Oct. 1996;9(10):2026-30.
Shevchenko et al., Peptide sequencing by mass spectrometry for homology searches and cloning of genes. J Protein Chem. Jul. 1997;16(5):481-90.
Stalmach et al., Identification of urinary peptide biomarkers associated with rheumatoid arthritis. PLoS One. Aug. 21, 2014;9(8):e104625.
Tekle et al., Defaulting from DOTS and its determinants in three districts of Arsi Zone in Ethiopia. Int J Tuberc Lung Dis. Jul. 2002;6(7):573-9.
Tucker et al., Point-of-care testing for sexually transmitted infections: recent advances and implications for disease control. Curr Opin Infect Dis. Feb. 2013;26(1):73-9.
Tyo et al., Low-Cost Healthcare Diagnostics by Directed Evolution of Peptide Receptors in Yeast. Poster presented at Synthetic Biology: Engineering, Evolution & Design (SEED), Boston, MA, Jun. 10-13, 2015. 1 page.
Venkatakrishnan et al. Molecular signatures of G-protein-coupled receptors. Nature. Feb. 14, 2013;494(7436):185-9.
Weigl et al., Point-of-Care Diagnostics in Low-Resource Settings and Their Impact on Care in the Age of the Noncommunicable and Chronic Disease Epidemic. J Lab Autom. Jun. 2014;19(3):248-57.
Young et al., The identification of tuberculosis biomarkers in human urine samples. Eur Respir J. Jun. 2014;43(6):1719-29.
International Search Report and Written Opinion for PCT/US2015/039996, dated Nov. 2, 2015. 17 Pages.

\* cited by examiner

FIG. 6A

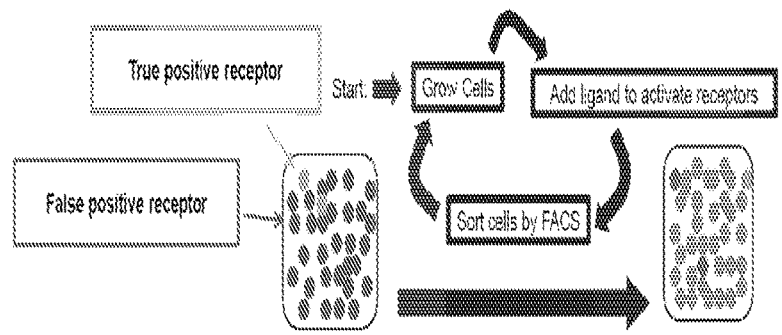

Goal: Enrich population for desired receptors using successive rounds of FACS to overcome single round false positive and false negative rates Bayes' analysis tells the number of sorting rounds required to confidently find true positive receptors at an initially defined frequency.

Bayes' Law applied to this system is: $P(+|D) = \dfrac{P(+)P(D|+)}{P(+)P(D|+) + P(-)P(D|-)}$ where:

| | Probability of... |
|---|---|
| P(+|D) | A true positive receptor has been detected |
| P(+) | True positive receptor |
| P(-) | False positive receptor |
| P(D|+) | Detecting a true positive receptor |
| P(D|-) | Detecting a false positive receptor |

Bayes' analysis was experimentally validated using different initial ratios of true to false positive receptors. True positive cells were confirmed with colony PCR.

*Cys1 peptide*

SEQUENCE LISTING

```
<160> NUMBER OF SEQ ID NOS: 15

<210> SEQ ID NO 1
<211> LENGTH: 13
<212> TYPE: PRT
<213> ORGANISM: Saccharomyces cerevisiae

<400> SEQUENCE: 1

Trp His Trp Leu Gln Leu Lys Pro Gly Gln Pro Met Tyr
1               5                   10

<210> SEQ ID NO 2
<211> LENGTH: 13
<212> TYPE: PRT
<213> ORGANISM: Artificial sequence
<220> FEATURE:
<223> OTHER INFORMATION: Synthetic peptide

<400> SEQUENCE: 2

Trp Ala Trp Leu Gln Leu Lys Pro Gly Gln Pro Met Tyr
1               5                   10

<210> SEQ ID NO 3
<211> LENGTH: 13
<212> TYPE: PRT
<213> ORGANISM: Artificial sequence
<220> FEATURE:
<223> OTHER INFORMATION: Synthetic peptide

<400> SEQUENCE: 3

Trp His Tyr Leu Gln Leu Lys Pro Gly Gln Pro Met Tyr
1               5                   10

<210> SEQ ID NO 4
<211> LENGTH: 12
<212> TYPE: PRT
<213> ORGANISM: Artificial sequence
<220> FEATURE:
<223> OTHER INFORMATION: Cystatin chimera

<400> SEQUENCE: 4

His Ala Leu Ala Leu Lys Pro Gly Glu Pro Met Tyr
1               5                   10
```

<210> SEQ ID NO 5
<211> LENGTH: 11
<212> TYPE: PRT
<213> ORGANISM: Artificial sequence
<220> FEATURE:
<223> OTHER INFORMATION: Cystatin chimera

<400> SEQUENCE: 5

Ala Leu Ala Leu Lys Pro Gly Glu Pro Met Tyr
1               5                   10

<210> SEQ ID NO 6
<211> LENGTH: 15
<212> TYPE: PRT
<213> ORGANISM: Artificial sequence
<220> FEATURE:
<223> OTHER INFORMATION: GSS chimera

<400> SEQUENCE: 6

Trp His Trp Leu Gln Leu Lys Pro Gly Glu Pro Leu Tyr Gly Arg
1               5                   10                  15

<210> SEQ ID NO 7
<211> LENGTH: 11
<212> TYPE: PRT
<213> ORGANISM: Artificial sequence
<220> FEATURE:
<223> OTHER INFORMATION: Cystatin chimera

<400> SEQUENCE: 7

Ala Leu Asp Phe Lys Pro Gly Glu Pro Met Tyr
1               5                   10

<210> SEQ ID NO 8
<211> LENGTH: 11
<212> TYPE: PRT
<213> ORGANISM: Artificial sequence
<220> FEATURE:
<223> OTHER INFORMATION: Cystatin chimera

<400> SEQUENCE: 8

Ala Leu Asp Leu Ala Val Gly Glu Pro Met Tyr
1               5                   10

<210> SEQ ID NO 9
<211> LENGTH: 11
<212> TYPE: PRT
<213> ORGANISM: Artificial sequence
<220> FEATURE:
<223> OTHER INFORMATION: Cystatin chimera

<400> SEQUENCE: 9

Ala Leu Asp Phe Ala Val Gly Glu Tyr Asn Lys
1               5                   10

<210> SEQ ID NO 10
<211> LENGTH: 13
<212> TYPE: PRT
<213> ORGANISM: Artificial sequence
<220> FEATURE:
<223> OTHER INFORMATION: GSS chimera

<400> SEQUENCE: 10

Leu His Leu Leu Ala Leu Lys Pro Gly Gln Pro Met Tyr
1               5                   10

```
<210> SEQ ID NO 11
<211> LENGTH: 15
<212> TYPE: PRT
<213> ORGANISM: Artificial sequence
<220> FEATURE:
<223> OTHER INFORMATION: GSS chimera

<400> SEQUENCE: 11

Leu His Leu Leu Ala Leu Lys Pro Gly Gln Pro Leu Tyr Gly Arg
1               5                   10                  15

<210> SEQ ID NO 12
<211> LENGTH: 15
<212> TYPE: PRT
<213> ORGANISM: Artificial sequence
<220> FEATURE:
<223> OTHER INFORMATION: GSS chimera

<400> SEQUENCE: 12

Leu His Leu Leu Ala Gly Gln Pro Gly Glu Ser Leu Tyr Gly Arg
1               5                   10                  15

<210> SEQ ID NO 13
<211> LENGTH: 15
<212> TYPE: PRT
<213> ORGANISM: Artificial sequence
<220> FEATURE:
<223> OTHER INFORMATION: GSS chimera

<400> SEQUENCE: 13

Leu Leu Leu Leu Ala Gly Gln Pro Glu Glu Ser Leu Ala Gly Arg
1               5                   10                  15

<210> SEQ ID NO 14
<211> LENGTH: 431
<212> TYPE: PRT
<213> ORGANISM: Saccharomyces cerevisiae

<400> SEQUENCE: 14

Met Ser Asp Ala Ala Pro Ser Leu Ser Asn Leu Phe Tyr Asp Pro Thr
1               5                   10                  15

Tyr Asn Pro Gly Gln Ser Thr Ile Asn Tyr Thr Ser Ile Tyr Gly Asn
            20                  25                  30

Gly Thr Thr Ile Thr Phe Asp Glu Leu Gln Gly Leu Val Asn Ser Thr
        35                  40                  45

Val Thr Gln Ala Ile Met Phe Gly Val Arg Cys Gly Ala Ala Ala Leu
    50                  55                  60

Thr Leu Ile Val Met Trp Met Thr Ser Arg Ser Arg Lys Thr Pro Ile
65                  70                  75                  80

Phe Ile Ile Asn Gln Val Ser Leu Phe Leu Ile Ile Leu His Ser Ala
                85                  90                  95

Leu Tyr Phe Lys Tyr Leu Leu Ser Asn Tyr Ser Ser Val Thr Tyr Ala
            100                 105                 110

Leu Thr Gly Phe Pro Gln Phe Ile Ser Arg Gly Asp Val His Val Tyr
        115                 120                 125

Gly Ala Thr Asn Ile Ile Gln Val Leu Leu Val Ala Ser Ile Glu Thr
    130                 135                 140

Ser Leu Val Phe Gln Ile Lys Val Ile Phe Thr Gly Asp Asn Phe Lys
145                 150                 155                 160

Arg Ile Gly Leu Met Leu Thr Ser Ile Ser Phe Thr Leu Gly Ile Thr
                165                 170                 175
```

```
Thr Val Thr Met Tyr Phe Val Ser Ala Val Lys Gly Met Ile Val Thr
            180                 185                 190

Tyr Asn Asp Val Ser Ala Thr Gln Gly Lys Tyr Phe Asn Ala Ser Thr
        195                 200                 205

Ile Leu Leu Ala Ser Ser Ile Asn Phe Met Ser Phe Val Leu Val Val
    210                 215                 220

Lys Leu Ile Leu Ala Ile Arg Ser Arg Arg Phe Leu Gly Leu Lys Gln
225                 230                 235                 240

Phe Asp Ser Phe His Ile Leu Leu Ile Met Ser Cys Gln Ser Leu Leu
                245                 250                 255

Val Pro Ser Ile Ile Phe Ile Leu Ala Tyr Ser Leu Lys Pro Asn Gln
            260                 265                 270

Gly Thr Asp Val Leu Thr Thr Val Ala Thr Leu Leu Ala Val Leu Ser
        275                 280                 285

Leu Pro Leu Ser Ser Met Trp Ala Thr Ala Ala Asn Asn Ala Ser Lys
    290                 295                 300

Thr Asn Thr Ile Thr Ser Asp Phe Thr Thr Ser Thr Asp Arg Phe Tyr
305                 310                 315                 320

Pro Gly Thr Leu Ser Ser Phe Gln Thr Asp Ser Ile Asn Asn Asp Ala
                325                 330                 335

Lys Ser Ser Leu Arg Ser Arg Leu Tyr Asp Leu Tyr Pro Arg Arg Lys
            340                 345                 350

Glu Thr Thr Ser Asp Lys His Ser Glu Arg Thr Phe Val Ser Glu Thr
        355                 360                 365

Ala Asn Asp Ile Glu Lys Asn Gln Phe Tyr Gln Leu Pro Thr Pro Thr
    370                 375                 380

Ser Ser Lys Asn Thr Arg Ile Gly Pro Phe Ala Asp Ala Ser Tyr Lys
385                 390                 395                 400

Glu Gly Glu Val Glu Pro Val Asp Met Tyr Thr Pro Asp Thr Ala Ala
                405                 410                 415

Asp Glu Glu Ala Arg Lys Phe Trp Thr Glu Asp Asn Asn Asn Leu
            420                 425                 430

<210> SEQ ID NO 15
<211> LENGTH: 7067
<212> TYPE: DNA
<213> ORGANISM: Artificial sequence
<220> FEATURE:
<223> OTHER INFORMATION: Synthetic

<400> SEQUENCE: 15
aattcgatat caagcttatc gataccgtcg acctcgagtc atgtaattag ttatgtcacg    60
cttacattca cgccctcccc ccacatccgc tctaaccgaa aaggaaggag ttagacaacc   120
tgaagtctag gtccctattt attttttttat agttatgtta gtattaagaa cgttatttat   180
atttcaaatt tttctttttt ttctgtacag acgcgtgtac gcatgtaaca ttatactgaa   240
aaccttgctt gagaaggttt tgggacgctc gaaggcttta atttgcggcc ggtacccaat   300
tcgccctata gtgagtcgta ttacgcgcgc tcactggccg tcgttttaca acgtcgtgac   360
tgggaaaacc ctggcgttac ccaacttaat cgccttgcag cacatccccc tttcgccagc   420
tggcgtaata gcgaagaggc ccgcaccgat cgcccttccc aacagttgcg cagcctgaat   480
ggcgaatggc gcgacgcgcc ctgtagcggc gcattaagcg cggcgggtgt ggtggttacg   540
cgcagcgtga ccgctacact tgccagcgcc ctagcgcccg ctcctttcgc tttcttccct   600
tcctttctcg ccacgttcgc cggctttccc cgtcaagctc taaatcgggg gctcccttta   660
```

```
gggttccgat ttagtgcttt acggcacctc gaccccaaaa aacttgatta gggtgatggt    720
tcacgtagtg ggccatcgcc ctgatagacg gttttcgcc ctttgacgtt ggagtccacg    780
ttctttaata gtggactctt gttccaaact ggaacaacac tcaaccctat ctcggtctat    840
tcttttgatt tataagggat tttgccgatt tcggcctatt ggttaaaaaa tgagctgatt    900
taacaaaaat ttaacgcgaa ttttaacaaa atattaacgt ttacaatttc ctgatgcggt    960
attttctcct tacgcatctg tgcggtattt cacaccgcat agggtaataa ctgatataat   1020
taaattgaag ctctaatttg tgagtttagt atacatgcat ttacttataa tacagttttt   1080
tagttttgct ggccgcatct tctcaaatat gcttcccagc ctgcttttct gtaacgttca   1140
ccctctacct tagcatccct tccctttgca aatagtcctc ttccaacaat aataatgtca   1200
gatcctgtag agaccacatc atccacggtt ctatactgtt gacccaatgc gtctcccttg   1260
tcatctaaac ccacaccggg tgtcataatc aaccaatcgt aaccttcatc tcttccaccc   1320
atgtctcttt gagcaataaa gccgataaca aaatctttgt cgctcttcgc aatgtcaaca   1380
gtacccttag tatattctcc agtagatagg gagcccttgc atgacaattc tgctaacatc   1440
aaaaggcctc taggttcctt tgttacttct tctgccgcct gcttcaaacc gctaacaata   1500
cctgggccca ccacaccgtg tgcattcgta atgtctgccc attctgctat tctgtataca   1560
cccgcagagt actgcaattt gactgtatta ccaatgtcag caaattttct gtcttcgaag   1620
agtaaaaaat tgtacttggc ggataatgcc tttagcggct taactgtgcc ctccatggaa   1680
aaatcagtca agatatccac atgtgttttt agtaaacaaa ttttgggacc taatgcttca   1740
actaactcca gtaattcctt ggtggtacga acatccaatg aagcacacaa gtttgtttgc   1800
ttttcgtgca tgatattaaa tagcttggca gcaacaggac taggatgagt agcagcacgt   1860
tccttatatg tagctttcga catgatttat cttcgtttcc tgcaggtttt tgttctgtgc   1920
agttgggtta agaatactgg gcaatttcat gtttcttcaa cactacatat gcgtatatat   1980
accaatctaa gtctgtgctc cttccttcgt tcttccttct gttcggagat taccgaatca   2040
aaaaaatttc aaagaaaccg aaatcaaaaa aagaataaaa aaaaaaatga tgaattgaat   2100
tgaaaagctg tggtatggtg cactctcagt acaatctgct ctgatgccgc atagttaagc   2160
cagccccgac acccgccaac acccgctgac gcgccctgac gggcttgtct gctcccggca   2220
tccgcttaca gacaagctgt gaccgtctcc gggagctgca tgtgtcagag gttttcaccg   2280
tcatcaccga aacgcgcgag acgaaagggc ctcgtgatac gcctattttt ataggttaat   2340
gtcatgataa taatggtttc ttaggacgga tcgcttgcct gtaacttaca cgcgcctcgt   2400
atcttttaat gatggaataa tttgggaatt tactctgtgt ttatttattt ttatgttttg   2460
tatttggatt ttagaaagta aataaagaag gtagaagagt tacggaatga agaaaaaaaa   2520
ataaacaaag gtttaaaaaa tttcaacaaa aagcgtactt tacatatata tttattagac   2580
aagaaaagca gattaaatag atatacattc gattaacgaa agtaaaatg taaaatcaca    2640 ggattttcgt gtgtggtctt ctacacagac aagatgaaac aattcggcat taatacctga   2700
gagcaggaag agcaagataa aaggtagtat ttgttggcga tccccctaga gtcttttaca   2760
tcttcggaaa acaaaaacta ttttttcttt aatttctttt tttactttct atttttaatt   2820 tatatatttta tattaaaaaa tttaaattat aattattttt atagcacgtg atgaaagga    2880 cccaggtggc acttttcggg gaatgtgcg cggaacccct atttgtttat ttttctaaat    2940
acattcaaat atgtatccgc tcatgagaca ataaccctga taaatgcttc aataatattg   3000
```

```
aaaaaggaag agtatgagta ttcaacattt ccgtgtcgcc cttattccct tttttgcggc   3060
attttgcctt cctgttttg ctcacccaga aacgctggtg aaagtaaaag atgctgaaga    3120
tcagttgggt gcacgagtgg gttacatcga actggatctc aacagcggta agatccttga   3180
gagttttcgc cccgaagaac gttttccaat gatgagcact tttaaagttc tgctatgtgg   3240
cgcggtatta tcccgtattg acgccgggca agagcaactc ggtcgccgca tacactattc   3300
tcagaatgac ttggttgagt actcaccagt cacagaaaag catcttacgg atggcatgac   3360
agtaagagaa ttatgcagtg ctgccataac catgagtgat aacactgcgg ccaacttact   3420
tctgacaacg atcggaggac cgaaggagct aaccgctttt ttgcacaaca tgggggatca   3480
tgtaactcgc cttgatcgtt gggaaccgga gctgaatgaa gccataccaa acgacgagcg   3540
tgacaccacg atgcctgtag caatggcaac aacgttgcgc aaactattaa ctggcgaact   3600
acttactcta gcttcccggc aacaattaat agactggatg gaggcggata agttgcagg    3660 accacttctg cgctcggccc ttccggctgg ctggtttatt gctgataaat ctggagccgg   3720
tgagcgtggg tctcgcggta tcattgcagc actggggcca gatggtaagc cctcccgtat   3780
cgtagttatc tacacgacgg ggagtcaggc aactatggat gaacgaaata gacagatcgc   3840
tgagataggt gcctcactga ttaagcattg gtaactgtca gaccaagttt actcatatat   3900
actttagatt gatttaaaac ttcattttta atttaaaagg atctaggtga agatccttt    3960 tgataatctc atgaccaaaa tcccttaacg tgagttttcg ttccactgag cgtcagaccc   4020
cgtagaaaag atcaaaggat cttcttgaga tcctttttt ctgcgcgtaa tctgctgctt    4080
gcaaacaaaa aaccaccgc taccagcggt ggtttgtttg ccggatcaag agctaccaac    4140 tcttttccg aaggtaactg gcttcagcag agcgcagata ccaaatactg tccttctagt    4200
gtagccgtag ttaggccacc acttcaagaa ctctgtagca ccgcctacat acctcgctct   4260
gctaatcctg ttaccagtgg ctgctgccag tggcgataag tcgtgtctta ccgggttgga   4320
ctcaagacga tagttaccgg ataaggcgca gcggtcgggc tgaacggggg gttcgtgcac   4380
acagcccagc ttggagcgaa cgacctacac cgaactgaga tacctacagc gtgagctatg   4440
agaaagcgcc acgcttcccg aagggagaaa ggcggacagg tatccggtaa gcggcagggt   4500
cggaacagga gagcgcacga gggagcttcc agggggaaac gcctggtatc tttatagtcc   4560
tgtcgggttt cgccacctct gacttgagcg tcgatttttg tgatgctcgt caggggggcg   4620
gagcctatgg aaaaacgcca gcaacgcggc ctttttacgg ttcctggcct tttgctggcc   4680
ttttgctcac atgttctttc ctgcgttatc ccctgattct gtggataacc gtattaccgc   4740
ctttgagtga gctgataccg ctcgccgcag ccgaacgacc gagcgcagcg agtcagtgag   4800
cgaggaagcg gaagagcgcc caatacgcaa accgcctctc cccgcgcgtt ggccgattca   4860
ttaatgcagc tggcacgaca ggtttcccga ctggaaagcg ggcagtgagc gcaacgcaat   4920
taatgtgagt tacctcactc attaggcacc ccaggcttta cactttatgc ttccggctcc   4980
tatgttgtgt ggaattgtga gcggataaca atttcacaca ggaaacagct atgaccatga   5040
ttacgccaag cgcgcaatta accctcacta aagggaacaa aagctggagc tcagtttatc   5100
attatcaata ctcgccattt caaagaatac gtaaataatt aatagtagtg attttcctaa   5160
ctttatttag tcaaaaaatt agccttttaa ttctgctgta acccgtacat gcccaaaata   5220 ggggcgggt tacacagaat atataacatc gtaggtgtct gggtgaacag tttattcctg    5280
gcatccacta aatataatgg agcccgcttt ttaagctggc atccagaaaa aaaagaatc    5340 ccagcaccaa aatattgttt tcttcaccaa ccatcagttc ataggtccat tctcttagcg   5400
```

```
-continued caactacaga gaacaggggc acaaacaggc aaaaaacggg cacaacctca atggagtgat    5460
gcaacctgcc tggagtaaat gatgacacaa ggcaattgac ccacgcatgt atctatctca    5520
ttttcttaca ccttctatta ccttctgctc tctctgattt ggaaaaagct gaaaaaaaag    5580
gttgaaacca gttccctgaa attattcccc tacttgacta ataagtatat aaagacggta    5640
ggtattgatt gtaattctgt aaatctattt cttaaacttc ttaaattcta cttttatagt    5700
tagtctttt tttagtttta aaacaccaga acttagtttc gacggattct agaactagtg     5760
gatccaaaaa aatgtctgat gcggctcctt cattgagcaa tctattttat gatccaacgt    5820
ataatcctgg tcaaagcacc attaactaca cttccatata tgggaatgga tctaccatca    5880
ctttcgatga gttgcaaggt ttagttaaca gtactgttac tcaggccatt atgtttggtg    5940
tcagatgtgg tgcagctgct ttgactttga ttgtcatgtg gatgacatcg agaagcagaa    6000
aaacgccgat tttcattatc aaccaagttt cattgttttt aatcattttg cattctgcac    6060
tctattttaa atatttactg tctaattact cttcagtgac ttacgctctc accggatttc    6120
ctcagttcat cagtagaggt gacgttcatg tttatggtgc tacaaatata attcaagtcc    6180
ttcttgtggc ttctattgag acttcactgg tgtttcagat aaaagttatt ttcacaggcg    6240
acaacttcaa aaggataggt ttgatgctga cgtcgatatc tttcacttta gggattgcta    6300
cagttaccat gtattttgta agcgctgtta aaggtatgat tgtgacttat aatgatgtta    6360
gtgccaccca agataaatac ttcaatgcat ccacaatttt acttgcatcc tcaataaact    6420
ttatgtcatt tgtcctggta gttaaattga ttttagctat tagatcaaga agattccttg    6480
gtctcaagca gttcgatagt ttccatattt tactcataat gtcatgtcaa tctttgttgg    6540
ttccatcgat aatattcatc ctcgcataca gtttgaaacc aaaccaggga acagatgtct    6600
tgactactgt tgcaacatta cttgctgtat tgtctttacc attatcatca atgtgggcca    6660
cggctgctaa taatgcatcc aaaacaaaca caattacttc agactttaca acatccacag    6720
ataggtttta tccaggcacg ctgtctagct ttcaaactga tagtatcaac aacgatgcta    6780
aaagcagtct cagaagtaga ttatatgacc tatatcctag aaggaaggaa acaacatcgg    6840
ataaacattc ggaaagaact tttgtttctg agactgcaga tgatatagag aaaaatcagt    6900
tttatcagtt gcccacacct acgagttcaa aaaatactag gataggaccg tttgctgatg    6960
caagttacaa agagggagaa gttgaacccg tcgacatgta cactcccgat acggcagctg    7020
atgaggaagc cagaaagttc tggactgaag ataataataa tttatga               7067
```

YEAST-BASED BIOSENSOR

CROSS REFERENCE TO RELATED APPLICATIONS

The present application claims the priority to U.S. Provisional Patent Application No. 62/023,549, filed Jul. 11, 2014, which is incorporated by reference in its entirety.

STATEMENT REGARDING FEDERAL FUNDING

This invention was made with government support under grant number DGE1324585 awarded by the National Science Foundation. The government has certain rights in the invention.

FIELD

Provided herein are compositions comprising yeast-based biosensors (YBBs) and methods of use thereof. In particular, YBBs are provided for the detection and/or quantification of an analyte (e.g., peptide analyte) in a sample (e.g., a biological sample, environmental sample, etc.).

BACKGROUND

Low-cost, point-of-care (POC) diagnostics are an invaluable resource for screening, diagnoses, and treatment for a range of diseases. POC is useful as it allows immediate results, and allows frequent measurements, as it is low cost. POC exist for several important molecule groups: small molecules (colorimetric reactions), nucleic acids (nucleic acid amplification tests, NAATs), and full proteins (lateral flow sandwich immunoassays, e.g., pregnancy tests). However, there is currently a technology gap in POC diagnostics for peptides, which are useful biomarkers in serum and urine for a range of diseases. Sandwich Immunoassays, for example, cannot simultaneously bind a peptide with two antibodies, and are therefore not useful. Instead, peptide tests rely on hospital laboratories with long wait times (hours to days) and are typically more expensive.

SUMMARY

Provided herein are compositions and systems comprising yeast-based biosensors (YBBs) and methods of use thereof. In particular, YBBs are provided for the detection and/or quantification of an analyte (e.g., peptide analyte) in a sample (e.g., a biological sample, environmental sample, etc.).

In some embodiments, provided herein are diagnostic compositions, devices, and methods comprising yeast-based biosensors (YBBs) engineered to detect analytes (e.g., peptides (e.g., biomarker peptides, etc.), etc.). In some embodiments, YBBs comprise (a) recognition element (e.g., receptor (e.g., modified yeast receptor, etc.), etc.) on the exterior of the biosensor (e.g., for binding and or recognition of the analyte (e.g., peptide)), and (b) a reporter that signals binding or recognition of the analyte.

In some embodiments, a recognition element is a cell surface receptor. In some embodiments, a recognition element is a yeast receptor. In some embodiments, a recognition element is a G protein-coupled receptor (GPCR). In some embodiments, a recognition element is Ste2p (e.g., SEQ ID NO: 14 or a variant thereof). In some embodiments, a recognition element is a modified (e.g., mutated, chimeric, etc.) version of a cell surface receptor, yeast receptor, GPCR, Ste2p, etc. In some embodiments, a recognition element has been developed and/or identified to recognize and/or bind a specific analyte (e.g., peptide). In some embodiments, a recognition element is a receptor for a native analyte, the specificity and/or selectivity of which has been altered (e.g., by mutation, by directed evolution, by design, etc.). In some embodiments, a recognition element binds a desired analyte (e.g., specifically), and sends a signal downstream (e.g., via G-protein or another signal transduction mechanism) to the reporter upon analyte binding. In some embodiments, a recognition element exhibits modified analyte recognition functionality. Modified recognition functionality may comprise increased sensitivity (e.g., to native peptides, to non-native peptides, or other analytes), increased specificity (e.g., effectively decreased sensitivity for non-target peptides or other analytes), etc.

In some embodiments, a reporter comprises any suitable molecular entity that produces a detectable signal, or a change in detectable signal, in response to analyte binding to the recognition element. In some embodiments, a reporter comprises a promoter that is activated, inhibited, enhanced, or otherwise altered in response to an analyte binding to the recognition element. In some embodiments, a reporter further comprises a detectable element that is expressed by the promoter. In such embodiments, upon binding of the analyte to the recognition element, the level of expression from the promoter is altered, and the level of the detectable element produced by the YBB is therefore altered as well.

In some embodiments, provided herein are artificial cellular entities comprising a: (a) surface-exposed recognition element that binds a non-native peptide analyte; and (b) a reporter that produces a detectable signal in response to binding of the peptide analyte and the recognition element. In some embodiments, the artificial cellular entity is a yeast-based biosensor (YBB). In some embodiments, the artificial cellular entity comprises an engineered yeast cell. In some embodiments, the surface-exposed recognition element is a non-native, engineered receptor protein. In some embodiments, the surface-exposed recognition element is a modified yeast G protein-coupled receptor (GPCR). In some embodiments, the surface-exposed recognition element comprises the signal transduction functionality of a native yeast GPCR with modified analyte recognition functionality. In some embodiments, the surface-exposed recognition element induces a G-protein signal transduction cascade upon binding non-native peptide analyte. In some embodiments, the surface-exposed recognition element is a modified Ste2p receptor. In some embodiments, the surface-exposed recognition element binds a peptide fragment of gramicidin S synthetase 2 or cystatin C. In some embodiments, the surface-exposed recognition element does not bind native alpha factor. In some embodiments, the reporter comprises: (i) a promoter, and (ii) a detectable element under expression control of said promoter. In some embodiments, expression from said promoter is altered by signal transduction from said surface-exposed recognition element. In some embodiments, expression from said promoter is enhanced by signal transduction from said surface-exposed recognition element. In some embodiments, the detectable element is a luciferase or fluorescent protein. In some embodiments, the artificial cellular entity further comprises a control reporter that produces a detectable signal independent of binding of the peptide analyte and the recognition element. In some embodiments, relative change of detectable element relative to the control reporter is indicative of analyte binding by the recognition element.

In some embodiments, provided herein are yeast-based biosensor comprising a yeast cell expressing: (a) a recognition element that is a modified version of a native yeast cell-surface receptor, wherein the recognition element binds to a peptide analyte that is not a natural ligand for the native yeast cell-surface receptor; and (b) a reporter, expression of which is linked to binding of the recognition element to the peptide analyte. In some embodiments, the recognition element has at least 50% sequence identity (e.g., 50%, 55%, 60%, 65%, 70%, 75%, 80%, 85%, 90%, 95%, 99%, or any ranges therebetween), but less than 100% sequence identity, with the native yeast cell-surface receptor. In some embodiments, the recognition element has at least 50% sequence similarity (e.g., 50%, 55%, 60%, 65%, 70%, 75%, 80%, 85%, 90%, 95%, 99%, or any ranges therebetween) with the native yeast cell-surface receptor. In some embodiments, a recognition element has less than 50% sequence identity and/or similarity with a native yeast receptor (e.g., 0%, 5%, 10%, 15%, 20%, 25%, 30%, 35%, 40%, 45%, or any ranges therebetween). In some embodiments, the recognition element is a mutant version of Ste2p and binds to a peptide analyte having less than 50% sequence identity (e.g., 0%, 5%, 10%, 15%, 20%, 25%, 30%, 35%, 40%, 45%, or any ranges therebetween) with α-factor. In some embodiments, provided herein are methods of detecting a peptide analyte in a sample, comprising exposing the yeast-based biosensor to the sample, and detecting expression of the reporter, wherein increased expression of the reporter indicates the presence of the peptide bioagent in the sample.

In some embodiments, provided herein are methods of detecting a peptide analyte in a sample, comprising: (a) contacting a sample with the artificial cellular entity described herein; and (b) detecting the detectable signal from said reporter. In some embodiments, methods further comprise comparing the detectable signal from said reporter to a control signal. In some embodiments, the control signal is the detectable signal from said reporter before contacting the sample with the artificial cellular entity. In some embodiments, the sample is an environmental, biological, security, or forensic sample. In some embodiments, the sample is a biological sample selected from blood, a blood product, urine, and saliva.

In some embodiments, provided herein are devices/systems comprising the artificial cellular entities (e.g., YBBs) described herein, and components for one or more of: storing the artificial cellular entities, combining the artificial cellular entities with a sample, mixing, detecting signal, quantifying signal, presenting results, etc.

In some embodiments, provided herein are compositions comprising artificial cellular entities comprising: (a) a first surface-exposed recognition element that binds a first non-native peptide analyte; (b) a second surface-exposed recognition element that binds a second non-native peptide analyte; and (c) a first reporter that produces a detectable signal in response to binding of the first peptide analyte and the first recognition element. In some embodiments, the first reporter also produces a detectable signal in response to binding of the second peptide analyte and the second recognition element. In some embodiments, compositions further comprise a second reporter that produces a detectable signal in response to binding of the second peptide analyte and the second recognition element. In some embodiments, the first and second reporters produce distinguishable detectable signals.

In some embodiments, provided herein are compositions comprising artificial cellular entities comprising: (a) a first surface-exposed recognition element that binds a non-native peptide analyte; (b) a second surface-exposed recognition element that binds the non-native peptide analyte; and (c) a first reporter that produces a detectable signal in response to binding of the peptide analyte and the first recognition element; wherein the first recognition element has a greater sensitivity for the peptide analyte than the second peptide analyte. In some embodiments, the first reporter also produces a detectable signal in response to binding of the peptide analyte and the second recognition element. In some embodiments, compositions further comprise a second reporter that produces a detectable signal in response to binding of the peptide analyte and the second recognition element. In some embodiments, the first and second reporters produce distinguishable detectable signals.

BRIEF DESCRIPTION OF THE DRAWINGS

FIGS. 6A and 6B show exemplary high-throughput screening methods.

DEFINITIONS

Figure 1:
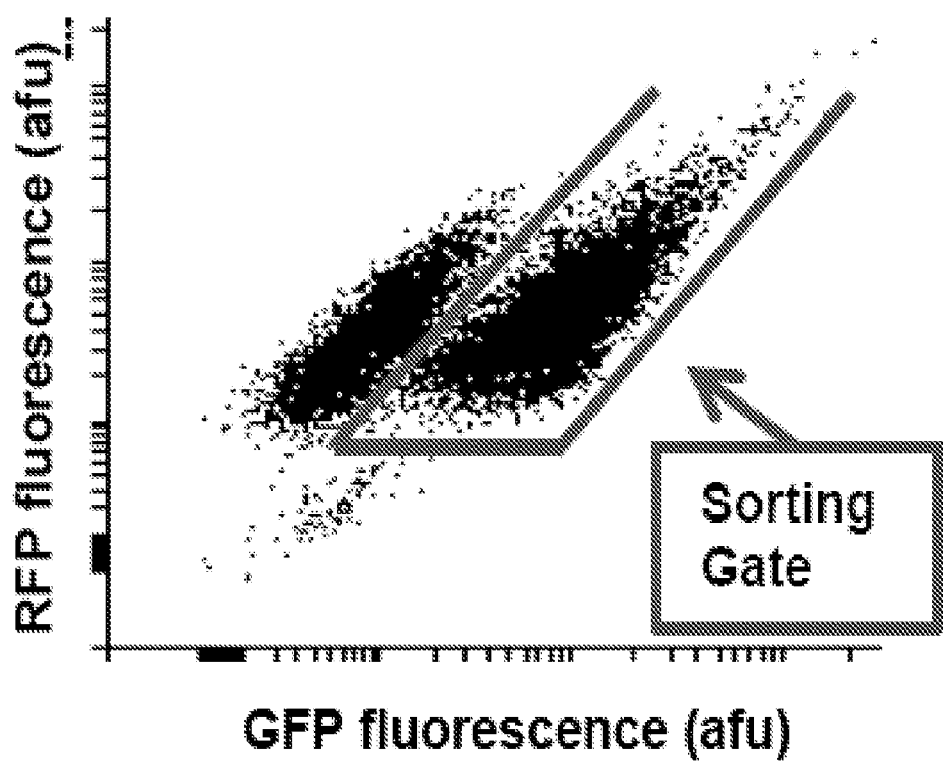
FIG. 1 shows population of Induced Ste2 receptors used to determine the gate for FACS.

As used herein, the term "artificial cellular entity" refers to a modified or engineered cell-derived entity with one or more additional, substituted, or removed components from its non-engineered ancestral cell. For example, a yeast-based biosensor is an artificial cellular entity derived from an ancestral yeast cell (e.g., by introduction of a modified receptor protein and a reporter).

As used herein the term "native receptor" refers to a ligand-binding protein of a cellular entity (e.g., located on the cell surface) that is also expressed by a non-engineered ancestral cell of the cellular entity. The native receptor on the cellular entity binds a ligand recognized or bound by the native receptor of the ancestral cell.

As used herein the term "non-native receptor" refers to a ligand-binding protein of an artificial cellular entity (e.g., located on the cell surface) that is not present in/on an ancestral cell of the artificial cellular entity. The non-native receptor on the artificial cellular entity typically binds a ligand not recognized or bound by native receptors of the ancestral cell. "Non-native receptors" may be receptors that are native to another cell type, a chimera of a native receptor and a receptor native to another cell type, a mutated native receptor (e.g., having various amino acid substitutions, deletions, and/or additions), an engineered receptor (e.g., a receptor that is not native to any cell), a chimera of a native receptor and an engineered receptor, etc.

As used herein, the term "analyte" refers to a molecular constituent of a sample (e.g., biological sample, environmental sample, etc.) that can be detected, quantified, and/or analyzed by appropriate methods. Analytes can include naturally occurring substances, artificial substances, metabolites, reaction products. Exemplary analytes include small molecules, nucleic acids, proteins, polypeptides, peptides, lipids, carbohydrates, etc. An analyte may be a ligand (e.g., peptide ligand) for a cell surface receptor (e.g., native receptor or modified receptor).

As used herein, the term "native analyte" refers to a molecular constituent of a sample that is recognized by a native receptor of a particular cell or cellular entity. Conversely, the term "non-native analyte" refers herein to a molecular constituent of a sample that is not recognized by a native receptor of a particular cell or cellular entity. However, a "non-native analyte" may, in some embodiments, be recognized or bound by a non-native receptor of an artificial cellular entity.

As used herein, the terms "polypeptide" and "peptide" refer to chains of amino acids linked by amide bonds between the carboxyl and amino groups of adjacent amino acids. "Peptide" refers to 29 or fewer amide bond-linked amino acids. "Polypeptide" refers to 30 or more amide bond-linked amino acids.

The term "reporter" is used herein in the broadest sense to describe a molecular entity, a characteristic and/or property of which (e.g., concentration, amount, expression, activity, cellular post-translational modification, localization, etc.) can be detected and correlated with a characteristic and/or property of a system containing the reporter (e.g., cell, artificial cellular entity, etc.). A "reporter" may be an intrinsic (e.g., endogenous) element of the system that exhibits one or more detectable and correlatable properties, or an artificial (e.g., exogenous) element engineered or introduced into the system (e.g., artificial cellular entity), that exhibits a detectable characteristic linked to process (e.g., gene expression) or component within the system. Suitable reporters include, but are not limited to: intrinsic genes or proteins (e.g., expression, concentration, activity, or protein-protein interactions of which may be correlated to a particular stimuli), exogenous genes or proteins (e.g., expression, concentration, activity, or protein-protein interactions of which may be correlated to a particular stimuli), luciferases, a beta lactamases, CAT, SEAP, a fluorescent proteins, etc.

As used herein, the term "wild-type," refers to a gene or gene product (e.g., protein) that has the characteristics (e.g., sequence) of that gene or gene product isolated from a naturally occurring source, and is most frequently observed in a population. In contrast, the term "mutant" refers to a gene or gene product that displays modifications in sequence when compared to the wild-type gene or gene product. It is noted that "naturally-occurring mutants" are genes or gene products that occur in nature, but have altered sequences when compared to the wild-type gene or gene product; they are not the most commonly occurring sequence. "Synthetic mutants" are genes or gene products that have altered sequences when compared to the wild-type gene or gene product and do not occur in nature. Mutant genes or gene products may be naturally occurring sequences that are present in nature, but not the most common variant of the gene or gene product, or "synthetic," produced by human or experimental intervention.

A "conservative" amino acid substitution refers to the substitution of an amino acid in a polypeptide with another amino acid having similar properties, such as size or charge. In certain embodiments, a polypeptide comprising a conservative amino acid substitution maintains at least one activity of the unsubstituted polypeptide. A conservative amino acid substitution may encompass non-naturally occurring amino acid residues, which are typically incorporated by chemical peptide synthesis rather than by synthesis in biological systems. These include, but are not limited to, peptidomimetics and other reversed or inverted forms of amino acid moieties. Naturally occurring residues may be divided into classes based on common side chain properties, for example: hydrophobic: norleucine, Met, Ala, Val, Leu, and Ile; neutral hydrophilic: Cys, Ser, Thr, Asn, and Gln; acidic: Asp and Glu; basic: His, Lys, and Arg; residues that influence chain orientation: Gly and Pro; and aromatic: Trp, Tyr, and Phe. Non-conservative substitutions may involve the exchange of a member of one of these classes for a member from another class; whereas conservative substitutions may involve the exchange of a member of one of these classes for another member of that same class.

As used herein, the term "percent sequence identity" refers to the degree (e.g., 50%, 60%, 70%, 80%, 90%, 95%, 98%, 99%, etc.) to which two polymer sequences (e.g., peptide, polypeptide, nucleic acid, etc.) have the same sequential composition of monomer subunits. If two polymers have identical sequences (e.g., 100% sequence identity) they may be referred to herein as having "sequence identity." The term "percent sequence similarity" refers to the degree (e.g., 50%, 60%, 70%, 80%, 90%, 95%, 98%, 99%, etc.) with which two polymer sequences (e.g., peptide, polypeptide, nucleic acid, etc.) have similar polymer sequences. For example, similar amino acids are those that share the same biophysical characteristics and can be grouped into the families (see above). If two polymers have sequences that have monomers at each position that share the same biophysical characteristics they may be referred to herein as having "sequence similarity." The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

DETAILED DESCRIPTION

Provided herein are compositions comprising yeast-based biosensors (YBBs) and methods of use thereof. In particular, YBBs are provided for the detection and/or quantification of an analyte (e.g., peptide analyte) in a sample (e.g., a biological sample, environmental sample, etc.).

Figure 6B:
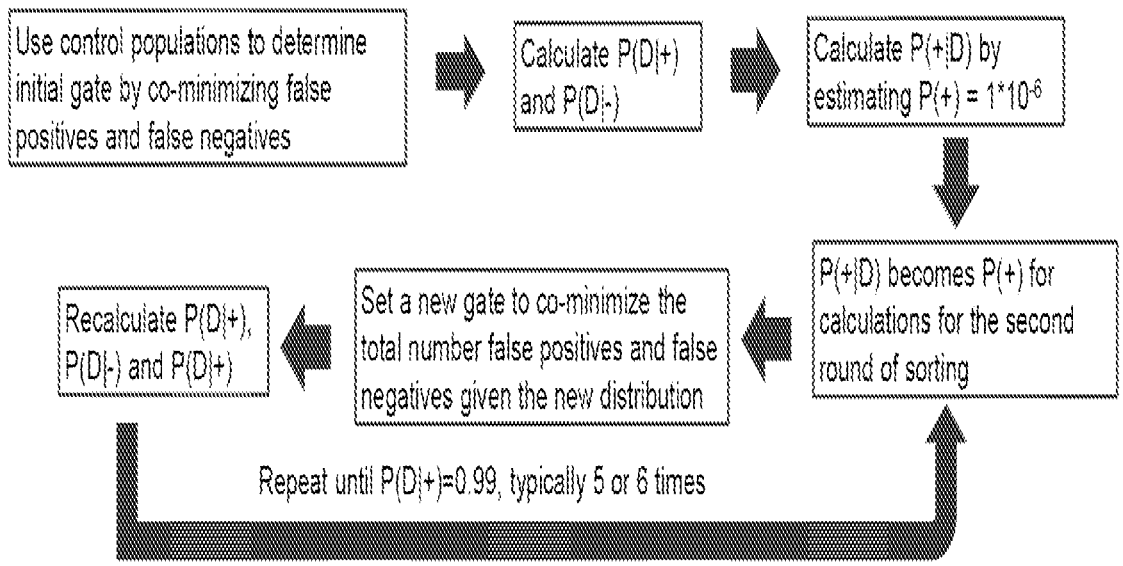
Figure 6B:
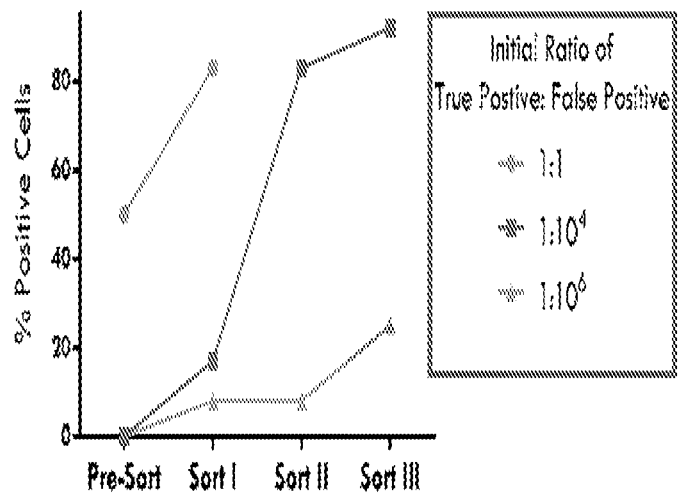

Yeast cells have great potential as a sensing element in biosensors due an outer membrane receptor with a highly evolvable structure. In some embodiments, introducing mutations to outer membrane receptors yields new detection capabilities (e.g., detection of non-native analytes). The ability to identify or engineer a non-native (e.g., mutant) receptor with novel detection capability (e.g., binding a non-native ligand) by previous methods was complicated by: (1) the large number of mutant receptors to be screened in order to find the desired detection capability, and (2) the presence of false negative and false positive receptors in a population of mutant receptors. Prior methods to screen mutant receptor libraries have unacceptable false positive rates. Experiments conducted during development of embodiments herein have demonstrated rigorous high-throughput screening methods to address this need (FIGS. 6A and 6B). Bayesian statistics account for false negative and false positive receptors and inform a flow cytometry-based sorting protocol to gradually eliminate false positive receptors from the population. These methods have successfully produced functional, mutant receptors with novel detection capabilities (e.g., for use in YBBs).

Experiments conducted during development of embodiments herein demonstrate the development of YBBs that take advantage of the yeast pheromone mating pathway, one of the best understood eukaryotic signaling pathways. Through this pathway, *Saccharomyces cerevisiae* detects mating pheromone with the Ste2 G-protein coupled membrane receptor (GPCR). Though *S. cerevisiae* has been used as a system to express heterologous mutagenized GPCRs, this research takes advantage of the native signaling machinery in yeast and eliminates the need for extensive pathway engineering that is often necessary for functional expression of heterologous receptors.

Experiments were conducted during development of embodiments herein to determine if a native receptor, in this case the Ste2 receptor, could be mutated to yield alternative detection capabilities (e.g., non-native ligand). Error-prone polymerase chain reaction was used to create a library of mutagenized Ste2 receptors. The library was searched for receptors that showed activity for variants of the native pheromone ligand. These variants differ from the native ligand by one amino acid, and the native Ste2 receptor shows little activity for these pheromone variants at physiological concentrations.

Results demonstrate successful identification of mutated receptors that respond to the pheromone variants. The library of mutant Ste2 receptors was sorted with fluorescence activated cell sorting (FACS). Developing a sorting protocol based on Bayesian statistics allowed us to minimize the amounts of false positive and false negative receptors in the mutant population. Receptor activation was indicated by green fluorescent protein (GFP) expression. The GFP value was normalized by red fluorescent protein (RFP), which was constitutively expressed. After FACS, individual mutant receptors were isolated from the population for characterization. Dose response curves were obtained by treating individual receptors with varying amounts of pheromone variant. EC50 values, the concentration of ligand at which half of the maximal response is obtained, were calculated for each isolated receptor.

For mutant receptors, the pheromone variant EC50 values obtained were significantly lower than those obtained with the native Ste2 receptor, implying that the isolated receptors are more sensitive than the native Ste2 receptor is for the pheromone variants. These results lay the foundation for future work for the directed evolution of the Ste2 receptor to detect non-native ligands.

Figure 5:
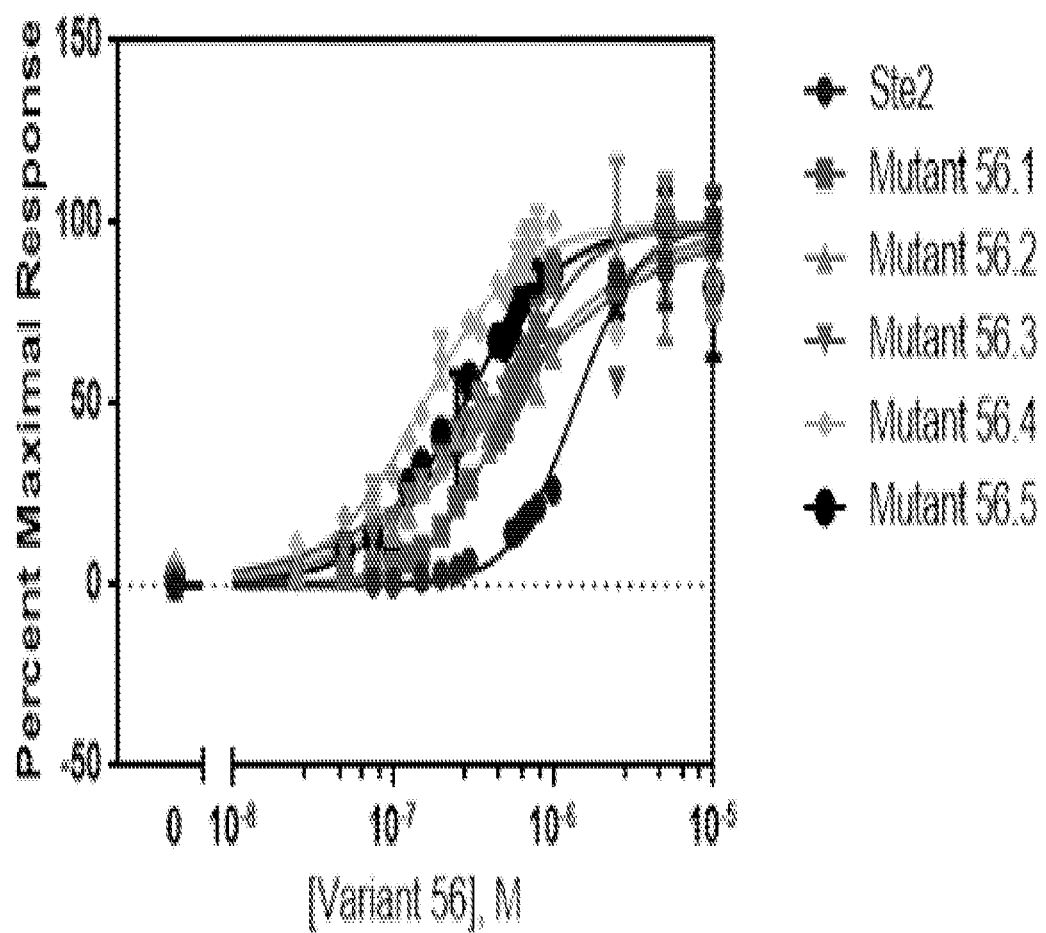
FIG. 5 shows dose response curves for Ste2 and mutant receptors. The EC50 values for mutants were significantly lower than the EC50 value for Ste2, implying that the mutants have increased sensitivity to Variant 56 as compared to the Ste2 receptor.

For example, error-prone polymerase chain reaction was used to create a library of mutagenized Ste2 receptors, and the library was searched for receptors that showed activity for a ligand variant 56 (SEQ ID NO: 3). The native Ste2 receptor showed little activity for Variant 56 as compared to the native ligand. The library of mutant Ste2 receptors was sorted with fluorescence activated cell sorting (FACS). Developing a sorting protocol based on Bayesian statistics minimized the amounts of false positive and false negative receptors in the mutant population. Receptor activation was indicated by GFP expression. The GFP value was normalized by RFP, which was constitutively expressed. After FACS, individual clones were isolated from the population for characterization. Dose response curves were obtained by treating individual receptors with varying amounts of Variant 56. The results (FIG. 5) demonstrate success in identifying mutated receptors that respond to Variant 56. EC50 values, the concentration of peptide at which half of the maximal response is obtained, were calculated for each isolated clone using GraphPad Prism software. For mutants, the EC50 value was significantly lower than that of the native Ste2 receptor, demonstrating that the isolated receptors are more sensitive than the native Ste2 receptor is for Variant 56. Results were repeatable for other variants.

In some embodiments, a biosensor comprises a microbe (e.g., a bacteria or yeast), or an artificial cellular entity derived therefrom. In particular embodiments, a biosensor comprises an artificial cellular entity based on or derived from a yeast cell. Suitable yeasts include, but are not limited to: *Pichia pastoris, Saccharomyces cerevisiae, Arxula adeninivorans (Blastobotrys adeninivorans), Candida boidinii, Hansenula polymorpha (Pichia angusta), Kluyveromyces lactis, Yarrowia lipolytica*, etc. For example, some YBBs comprise a whole yeast cell engineered to express: (1) a non-native receptor protein (e.g., one that recognizes an analyte of interest), (2) a reporter with activity, expression, etc. linked to binding of the analyte to the receptor, and (3) optionally a control reporter (e.g., not linked to binding of the analyte to the receptor).

In some embodiments, non-native proteins or other engineered elements (e.g., recognition element, reporter(s), etc.) are expressed in a yeast cell or yeast-derived artificial cellular entity under a constitutive promoter, inducible promoter, or a combination thereof. In some embodiments, suitable promoters include, but are not limited to: GAL1, GAL7, GAL10, Met25, CUP1, etc. In some embodiments, non-native proteins or other engineered elements are expressed on the same vector. In some embodiments, non-native elements are expressed under the control of the same type of promoter. In some embodiments, non-native elements are expressed behind the same promoter. In some embodiments, multiple non-native elements are expressed from different vectors. In some embodiments, multiple non-native elements are expressed under the control of different types of promoters. Embodiments described herein are not limited by the identity of the vector(s). Expression vectors may include: a regulatory sequences for protein expression such as promoter, enhancer, a terminator; a replication origin; and a selection marker such as URA3, LEU2, HIS3, TRP1, LYS2, etc. In some embodiments, non-native elements are incorporated as genes into the genome of a host cell (e.g., chromosomal intertion).

In some embodiments, systems and methods described herein comprise a recognition element that interacts with one or more analytes of interest. In some embodiments, the analyte of interest is a non-native analyte. In some embodiments, the recognition element is specific for a single analyte. In other embodiments, the recognition element binds multiple (e.g., 2, 3, 4, 5, 10, 20, 50, 100, or more) analytes. In some embodiments, the recognition element binds (e.g., covalently or non-covalently) the analyte. In some embodiments, the recognition element interacts with the analyte via hydrogen bonds, van der Waals, hydrophobic, and/or ionic interactions. In some embodiments, a recognition element is any suitable molecular entity capable of (1) interacting with an analyte of interest and (2) transducing a signal directly or indirectly (e.g., via G-protein and/or a signal cascade) to the reporter. In some embodiments, a signal from the recognition element to the reporter or an intermediary is turned on, turned off, enhanced, inhibited, or altered upon interaction of the recognition element with the analyte.

In some embodiments, a recognition element comprises at least an interaction moiety and a signaling moiety. The interaction moiety interacts (e.g., binds) the target analyte, and the signaling moiety signals the reporter (e.g., directly or indirectly (e.g., via G protein)).

In some embodiments, the recognition element is a cell surface receptor or transmembrane receptor protein. In some embodiments, the recognition element is a modified yeast receptor (e.g., evolved to recognize a non-native analyte while retaining signaling capability). In some embodiments, the recognition element is a chimeric version of a portion of a yeast receptor (e.g., the signaling moiety) with an engineered segment (e.g., non-native peptide or polypeptide). In some embodiments, the recognition element is a chimeric version of a portion of a yeast receptor with an engineered segment (e.g., the signaling moiety) with a portion of a non-yeast receptor (e.g., an interaction element that recognizes a target analyte not recognized by yeast).

In some embodiments in which a recognition element comprises a modified yeast receptor or a chimera comprising a portion that is a yeast receptor, the yeast receptor is a G protein-couple receptor (GPCR). In some embodiments, the recognition element comprises the transmembrane and/or signaling sequence and/or functionality of the original yeast GPCR with altered analyte recognition. In some embodiments, all or a portion of the recognition element comprises a non-yeast GPCR (e.g., from another species) that is capable of initiating signaling through G-protein in a yeast system (e.g., YBB). In some embodiments, a recognition element comprises portions (e.g., from a yeast GPCR, from a non-yeast GPCR) that have been engineered (e.g., modified, mutated, evolved, chimerized, etc.) to result in an artificial receptor.

Although embodiments herein are not limited to any particular recognition element, in some embodiments, recognition elements are derived from (e.g., via rational modification, chimerization, directed evolution, etc.) the yeast GPCR Ste2p. In some embodiments, the interaction moiety of Ste2p is modified to bind non-native analytes (e.g., peptides). In some embodiments, the signaling and/or transmembrane moieties of Ste2p are substantially unmodified (e.g., in terms of sequence and/or function), thereby retaining the capacity to transduce a signal via G protein.

In some embodiments, a YBB comprises multiple (e.g., 2, 3, 4, 5, 6, 7, 8, 9, 10, 15, 20, 30, 40, 50, 100, 200, 500, 1000, or more) recognition elements capable of recognizing multiple different analytes (e.g., peptides of unrelated sequence, peptides of similar sequences, etc.). In some embodiments, two or more (e.g., 2, 3, 4, 5, 6, 7, 8, 9, 10) different recognition elements (e.g., capable of recognizing different analytes) are linked (e.g., via a signal transduction pathway) to different reporters. In such a scheme, the presence and/or concentration of a particular analyte can be determined based on a correlation with the particular reporter associated with the recognition element for that reporter. In other embodiments, two or more (e.g., 2, 3, 4, 5, 6, 7, 8, 9, 10, 15, 20, 30, 40, 50, 100, 200, 500, 1000, or more) different recognition elements (e.g., capable of recognizing different analytes) are linked (e.g., via a signal transduction pathway) to the same reporter. In such a scheme, the presence and/or concentration of any or all of the analytes can be determined based on a correlation with the reporter.

In some embodiments, systems and methods described herein comprise a reporter that signals binding or recognition of the analyte to the recognition element. A reporter is any suitable molecular entity that is capable of signaling (e.g., quantitatively or qualitatively) binding or recognition of the analyte to the recognition element. The signal may be a change in expression, concentration, activity, etc. Suitable reporters include fluorescent proteins (e.g., GFP, YFP, CFP, BFP, RFP and any variants thereof [see e.g., U.S. Pat. Nos. 5,804,387; 6,090,919; 6,096,865; 6,054,321; 5,625,048; 5,874,304; 5,777,079; 5,968,750; 6,020,192 and 6,146,826; and published international patent application WO 99/6459; each of which is herein incorporated by reference in its entirety), photoproteins (e.g., aequorin or obelin); various enzymes including luciferases, β-lactamase, dihydrofolate reductase, beta-galactosidase, tyrosinase, neomycin or hygromycin phosphotransferase, and a wide range of other enzymes. In some embodiments, the reporter comprises a gene coding for a protein selected from the group consisting of a luciferase, a beta lactamase, CAT, SEAP, a fluorescent protein, or a quantifiable gene product. In some embodiments, the reporter is a fluorescent or bioluminescent reporter. In certain embodiments, a bioluminescent reporter is a luciferase. In some embodiments, a luciferase is selected from those found in *Omphalotus olearius*, fireflies (e.g., *Photinini*), *Renilla reniformis*, mutants thereof, portions thereof, variants thereof. Embodiments described herein are not limited by the potential identity of the reporter.

In some embodiments, a reporter comprises post-translational event for signaling. For example, a quenched fluorescent protein is activated (e.g., unquenched) upon cleavage by a In some embodiments, the subcellular localization of a protein or other reporter is altered upon analyte binding to the recognition element.

In some embodiments, a YBB comprises both a recognition reporter (a characteristic (e.g., activity, concentration, expression, etc.) of which is linked to recognition/binding of an analyte to the recognition element) and a control reporter (not linked to recognition/binding of an analyte to the recognition element). In such cases, the ratio of recognition reporter to control reporter (or control reporter to recognition reporter) provides a measure (e.g., quantitative measure) of analyte binding to the recognition element that is controlled for other changes to the sample. The control reporter and recognition reporter may be any two independent reporters.

In some embodiments, a YBB comprises multiple reporters (e.g., recognition reporters). In some embodiments, multiple different reporters are each associated with different recognition elements (e.g., directly or via a signal transduction pathway). In some embodiments comprising multiple reporters, the signals from said reporters are distinguishable (e.g., via appropriate detection technologies).

In some embodiments, the analyte is any molecular or macromolecular entity capable of being bound, or otherwise interacted with, by the recognition element such that a signaling between the recognition element and the reporter is altered (e.g., turned on, turned off, enhanced, inhibited, etc.). In some embodiments, the analyte is a protein, polypeptide, peptide, nucleic acid (e.g., DNA (e.g., a particular DNA sequence), RNA (e.g., miRNA, siRNA, snRNA, snoRNA, piRNA, aRNA, mRNA, etc.), peptide nucleic acid, etc.), lipid, carbohydrate, small molecule, etc. In particular embodiments, the analyte is a peptide. In some embodiments, an analyte is a peptide between 3 and 29 amino acids in length (e.g., 3, 4, 5, 6, 7, 8, 9, 10, 11, 12, 13, 14, 15, 16, 17, 18, 19, 20, 21, 22, 23, 24, 25, 26, 27, 28, 29, or any ranges therebetween (e.g., 5-20, 8-15, 6-18, etc.)).

In some embodiments, the analyte is a peptide fragment of a larger protein or polypeptide. Any known method for fragmenting a protein or polypeptide may find use in embodiments herein (e.g., chemical digestion, enzymatic digestion, etc.). It is possible to digest the polypeptide either enzymatically or chemically to produce fragments thereof. In some embodiments, a technique is selected that will produce a fragment that is an analyte for the recognition element. Therefore, by detection of the peptide fragment, the presence or concentration of the larger protein or polypeptide is determined. In some embodiments, a biosensor comprises recognition elements for multiple fragments of a protein. A polypeptide may be digested enzymatically, e.g. using trypsin, endoproteinase Lys C, endoproteinase Arg C, or chymotrypsin. Alternatively, chemical digestion can be used, such as by cyanogen bromide. (For a general reference to digestion methods, see e.g. U.S. Pat. No. 5,821,063; herein incorporated by reference in its entirety).

In some embodiments, provided herein are methods of generating biosensors (e.g., YBBs) for a target analyte (e.g., peptide of interest).

In some embodiments, an existing yeast receptor (e.g., GPCR (e.g., Ste2p)) is modified (e.g., rationally, directed evolution, etc.) to generate a recognition element capable of interacting with (e.g., binding) a target analyte. Any methods of modifying a native yeast receptor may find use herein. For example, as detailed herein, in some embodiments, directed evolution techniques (e.g., multiple iterations, using one or more intermediate analytes, etc.) allow for the generation of a recognition element capable of recognizing a non-native analyte (e.g., peptide) of interest while maintaining the signal transduction functionality of the native receptor. In other embodiments, a non-native interaction moiety (e.g., from another receptor, engineered, etc.) is substituted for the interaction moiety of a native yeast receptor.

In some embodiments, a reporter is introduced into a biosensor under the control of signaling from the recognition element (e.g., direct control, indirect control (e.g., via signal transduction pathway, etc.), etc.)

In some embodiments, non-native elements (e.g., reporter, recognition element, etc.) are introduced into a host cell via known methods (e.g., transfection) and using known molecular biology tools (e.g., vectors). In some embodiments, a host cell (e.g., yeast) is stably transfected to generate a YBB that expresses the desired non-native elements (e.g., reporter and recognition element). In some embodiments, non-native elements are integrated into the genome of the host cell (e.g., chromosomal integration).

In some embodiments, provided herein are methods of detecting and/or quantifying a target analyte (e.g., peptide of interest) in a sample (e.g., biological sample, environmental sample, etc.) using the biosensors (e.g., YBBs) described herein. In some embodiments, a YBB designed to detect one or more target analytes is added to a sample (e.g., biological, environmental, security, etc.), and signal (or absence thereof) from one or more reporters of the YBB is detected. In some embodiments, a ratio of one or more recognition reporters to one or more control reporters is used to detect and/or quantify one or more target analytes. In some embodiments, a sample is added to YBBs described herein. In some embodiments, a sample is added to system of device comprising YBBs. For example, a sample may be applied to a surface displaying one or more different YBBs. Detection of reporter signal on the surface indicates the presence or a threshold level of the target analyte. In other embodiments, a sample in introduced into a POC device (See, e.g., FIG. 10) within which one or more of sample processing, YBB introduction, and signal detection are performed.

In some embodiments, the YBBs described herein find use in detection of analytes in any suitable sample. A sample may be a solid, liquid or gas, and suitable processing techniques for such samples are understood in the field. A sample may be of biological, environmental, or man-made origin. In the case of biological samples, the sample may be a biological fluid such as the biological sample is selected from the group consisting of whole blood, plasma, serum, urine, sputum, saliva, nipple aspirate, ductal lavage, vaginal fluid, nasal fluid, ear fluid, gastric fluid, cerebrospinal fluid, sweat, pericrevicular fluid, semen, prostatic fluid, feces, cell lysate, tissue lysate, tears, etc. A biological sample may also comprise tissue, hair, skin, biopsy material, etc. In the case of environmental samples, the sample may be soil, dirt, sewage, air, water, plant material, etc. Manmade samples include, in particular forensic or security screening samples (e.g., clothing, luggage, etc.).

In some embodiments, reporter signal is detected using any appropriate assay. For example, in embodiments in which the reporter emits a light output (e.g., reporter is a luciferase or fluorescent protein), light is detected with, for example, a luminometer or fluorometer. In embodiments, in which the detectable signal is expression or release of a chemical or macromolecular entity, appropriate reagents (e.g., antibodies, etc.) are provided. In some embodiments, a POC device for detection of the analyte comprises appropriate detection components and/or reagents. In other embodiments, a POC device (or output therefrom) is applied to a detection device for signal detection.

Figure 10:
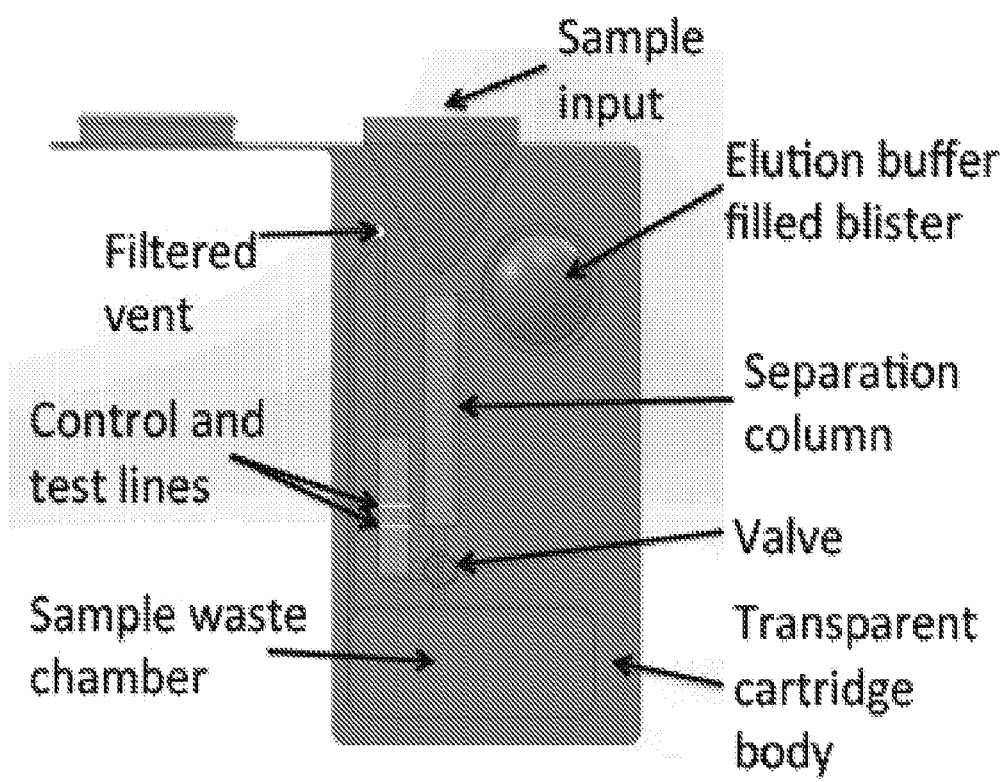
FIG. 10 shows an exemplary POC device comprising a YBB. Operation: [1] Sample is added and capped. [2] Sample wicks through a separation column where protein is cleaved by thermostable trypsin. [3] Peptides adhere to C18 column while bulk sample is wicked to waste chamber. [4] Elution buffer blister is burst, causing peptide release in small volume, which is subsequently exposed to YBB.

In some embodiments, artificial cellular entities are provided as biosensors (e.g., YBBs) within a system or device (e.g., POC system/device) configured for the detection of one or more analytes in a sample. In some embodiments, the system/device facilitates one or more of: reagent (e.g., YBB, buffers, etc.) storage, sample purification, introduction of the sample and biosensors, mixing, reaction, signal detection, signal quantification, communication of results (e.g., on a screen, on a printer report, etc.), etc. A system/device may be of any suitable configuration for carrying out the particular detection/quantification assay. An exemplary system/device is depicted in FIG. 10. A system/device may be specific for the detection of a single analyte (or set of analytes) or may be customizable according to the reagents (e.g., YBBs) used. A system/device may comprise a single unit, or multiple modules (e.g., regent module, mixing module, reaction module, detection module, etc.). In particular embodiments, a system/device is configured for point-of-care applications. Exemplary systems/devices, all or portions of which may find use in embodiments herein, are described, for example, in: U.S. Pat. No. 8,697,377; WO 2014/134537; U.S. Pat. No. 7,604,592; U.S. Pat. Pub. 2013/0210652; U.S. Pat. Pub. 2014/0320807; U.S. Pat. Nos. 8,523,797; 8,005,686; 8,283,155; 8,110,392; each of which is herein incorporated by reference in their entireties.

The biosensors described herein may find use is any suitable field. In medicine, devices/systems incorporating the YBBs described herein find use, for example: in hospitals and medical clinics for bedside/in-room detection of biomarkers (e.g., for quick and reliable detection/diagnosis of disease, pathogen, condition, etc.); for in-the-field detection of pathogens or diagnosis; etc. The devices/systems and/or biosensors herein may find use for the detection of pollutants or contaminants in an environmental sample (e.g., in the field where other more complicated systems are not practical). In security anti-terrorism applications (e.g., airport security, customs, etc.), the biosensors herein provide rapid, on-site detection of potential threats. In research, the biosensors herein find use, for example, in high throughput screening to search libraries of mutant proteins. The applications/uses described herein are not limiting.

The advantages of the biosensors (e.g., YBBs) and devices/systems described herein include, for example: low-cost, no specialized training to use, amenable to use in resource poor areas, does not require refrigeration, reduced false positives, etc.

In some embodiments, this technology provides a platform for the creation of yeast-based biosensors toward peptide ligands of interest that are affordable and require little specialized training to use. The technology takes advantage of a yeast membrane receptor that natively detects the alpha factor pheromone. The structure of the receptor is highly evolvable, making it amenable to detecting non-native ligands. Experiments were conducted during development of embodiments herein to create a library of mutant receptors which were screened for mutants with desired detection capabilities. In some embodiments, the screening method carefully considers the rates of false positives and false negatives that exist in a library of mutant receptors to determine the settings to be used in flow-cytometry based sorting protocol that gradually eliminates false positive receptors from the mutant library.

EXPERIMENTAL

Example 1

Evolution of Ste2 Membrane Receptor to Detect Non-Native Ligands

Knockout of Native Ste2 and Installation of Fluorescent Markers.

The parent strain for all experiments has the native Ste2 receptor removed from the genome. The STE2 gene, or mutants thereof, was incorporated on a plasmid with an auxotrophic marker. Yeast optimized GFP (yeGFP) was inserted into the FUS1 locus, a downstream target of pheromone pathway activation, and provides a green fluorescent marker to report binding events. RFP, a red fluorescent marker, was cloned in place of the TRP1 gene so that RFP is under constitutive regulation and consequently reflects natural variations in cell state, size, and protein production level. Pathway activation was therefore defined as GFP/RFP to account for natural variations in cell state.

Creation and Transformation of Mutant Ste2 Receptors

To create a library of mutant receptors, error prone PCR (epPCR) was performed on the native Ste2 receptor, and resulted in 0-6 base mutations/kb. Homologous recombination was used to introduce mutagenized receptors into yeast. The primers used for epPCR added 40 base pairs of homologous sequence on each side of the mutagenized gene. The sequences correspond to the regions flanking a linear fragment of DNA that served as the plasmid backbone and contained an auxotrophic marker. Thus, with the introduction of just the mutagenized gene and the linear backbone fragment, the yeast can construct a circular plasmid with a mutagenized receptor. Mutagenized Ste2 receptors were transformed into yeast using electroporation, and libraries of $10^5$-$10^8$ mutant receptors were obtained.

Ligand Library

Variants of the alpha factor pheromone were chemically synthesized. The native alpha pheromone sequence is: WHWLQLKPGQPMY (SEQ ID NO:1). The analysis of two variants, Variant 44 (WAWLQLKPGQPMY; SEQ ID NO:2) and Variant 56 (WHYLQLKPGQPMY; SEQ ID NO:3), is presented below. Variant 44 contains an alanine substitution at the second position, and Variant 56 contains a tyrosine substitution at the third position. Previous literature showed Ste2 had a very low response, if any, to Variants 44 and 56 at physiological concentrations.

Screening of Mutant Stet Receptor Library

The library of mutagenized Ste2 receptors was sorted with a FACS-based protocol informed by Bayesian statistics to account for receptor stochasticity. The stochastic nature of the Ste2 receptor is demonstrated when a population of *S. cerevisiae* with the native Ste2 receptor is induced with a saturating amount of alpha factor and GFP serves as a reporter molecule. The population is distributed bimodally, with distinct low and high fluorescing populations. However, the low fluorescing population of induced receptors overlaps with a population that has not been activated with alpha factor (FIG. 1). This demonstrates that the negotiation of accepting false negative receptors and losing false positive receptors should be addressed during FACS.

The stochasticity was addressed with Bayesian statistics, which accounts for the distribution of false positives and false negatives based on the population obtained from a previous sorting round. Bayes' law as applied to this system is:

$$P(+|D) = \frac{P(+)P(D|+)}{P(+)P(D|+) + P(-)(D|-)},$$

where:

| | Probability of . . . |
|---|---|
| P(+|D) | A true positive receptor has been detected |
| P(+) | True positive receptor |
| P(−) | False positive receptor |
| P(D|+) | Detecting a true positive receptor |
| P(D|−) | Detecting a false positive receptor |

Figure 2:
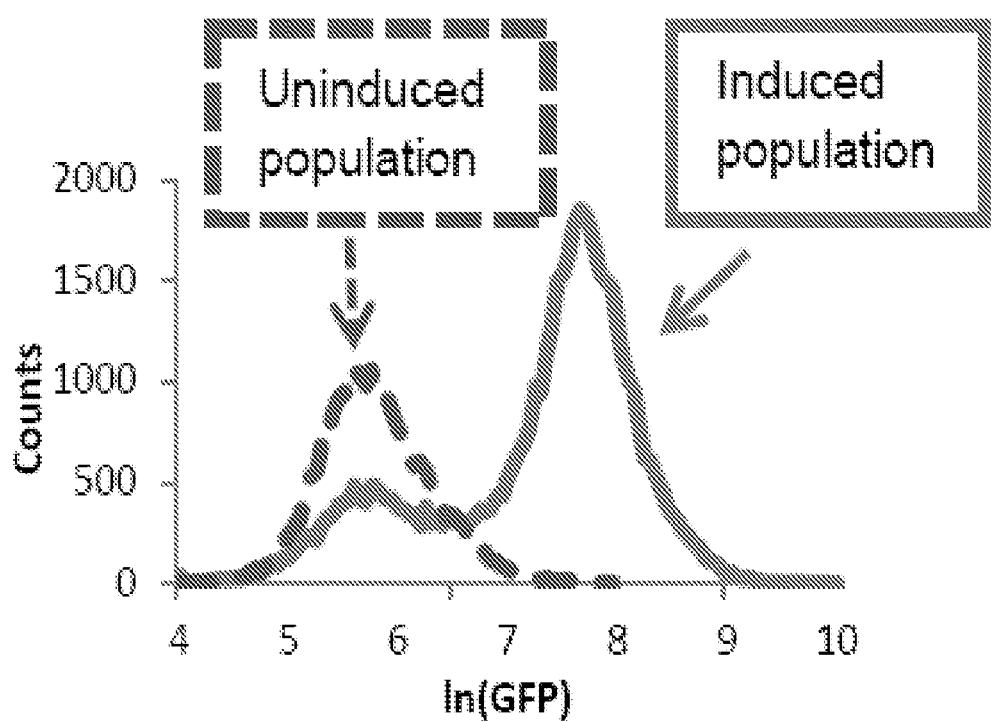
FIG. 2 shows stochasticity of a population of Ste2 receptors induced with alpha factor.

The initial GFP/RFP gate for FACS was based upon the distribution of a population of cells expressing the native Ste2 receptor that have been induced with 1 micromolar alpha factor, a saturating amount of ligand. The gate for FACS was determined by co-minimizing the ratios of false negative and false positive receptors in the population (FIG. 2). There was a natural separation between the low and high fluorescing populations such that the high fluorescing population typically comprises about 75% of the total induced population. This distribution was used to calculate the ratio of false negative receptors in a population. An uninduced population of native receptors was also examined using this gate. This distribution was used to calculate the ratio of false positive receptors in a population. Typically, less than 2% of cells from the uninduced population are within the gate. The gate and the distributions were used to calculate P(D|+), the probability of detecting a true positive receptor, and P(D|−), the probability of detecting a false positive receptor. For the first round of sorting, P(+), the probability of a true positive receptor, was estimated (usually to be $1*10^{-6}$), and P(−), the probability of a false positive, is equivalent to 1−P(+).P(+|D) for the first round was calculated. This value became P(+) for calculations for the second round of sorting. Given this new distribution and the number of cells to be run through the flow cytometer (typically set to be a 10-times over-sampling of the library size) a new gate is set to co-minimize the total number false positives and false negatives. The probabilities of detection: P(D|+) and P(D|−) were recalculated, allowing for P(D|+) to be calculated for the second round. This iterative calculation was performed until P(D|+)=0.99, which typically requires 5 or 6 rounds of sorting.

For each round of sorting, the mutagenized library was grown overnight and then diluted to an OD600=0.1. The ligand for which activity is to be evolved for was added at 100 nM immediately after dilution and the culture was incubated for 2.5 hours at 30° C. with 225 RPM shaking before being sorted by FACS. This sorted population was grown in selective media for 24-36 hours, until stationary phase was reached. The library was diluted again, and induced with ligand for another round of sorting by FACS. This process was repeated for six rounds to gradually eliminate false positive receptors from the population of mutagenized Ste2 receptors. The number of rounds was determined with Bayesian statistics as described above.

Characterization of Isolated Mutants for Improved Activity

Figure 3:
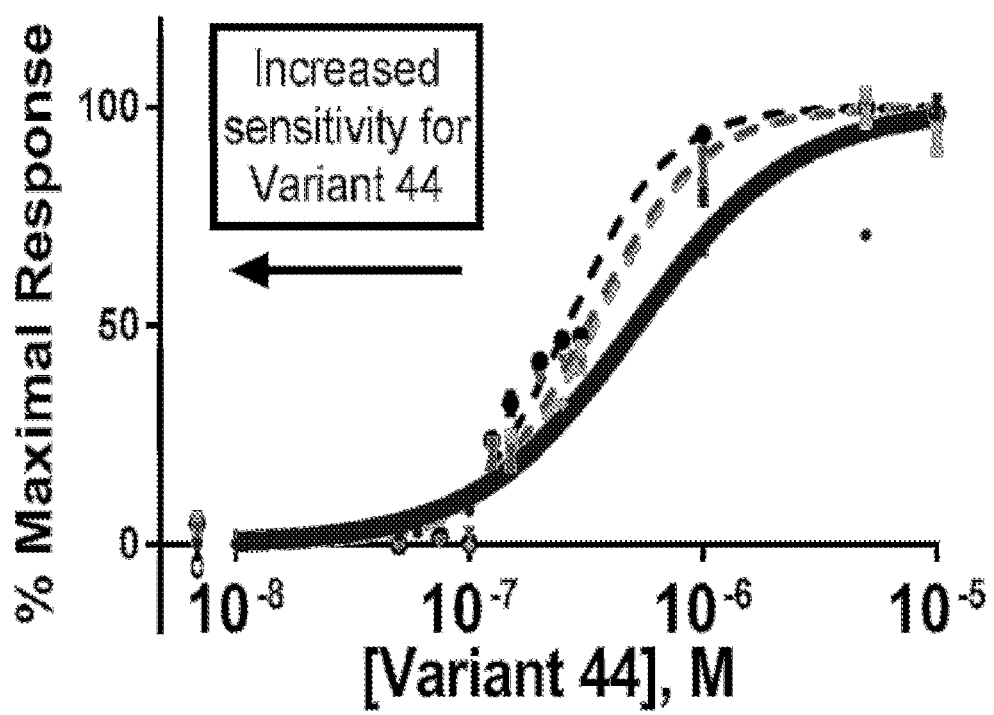
FIG. 3 shows dose response curves for mutants isolated for sensitivity to ligand variant 44 against Variant 44 and the native alpha factor.
Figure 3:
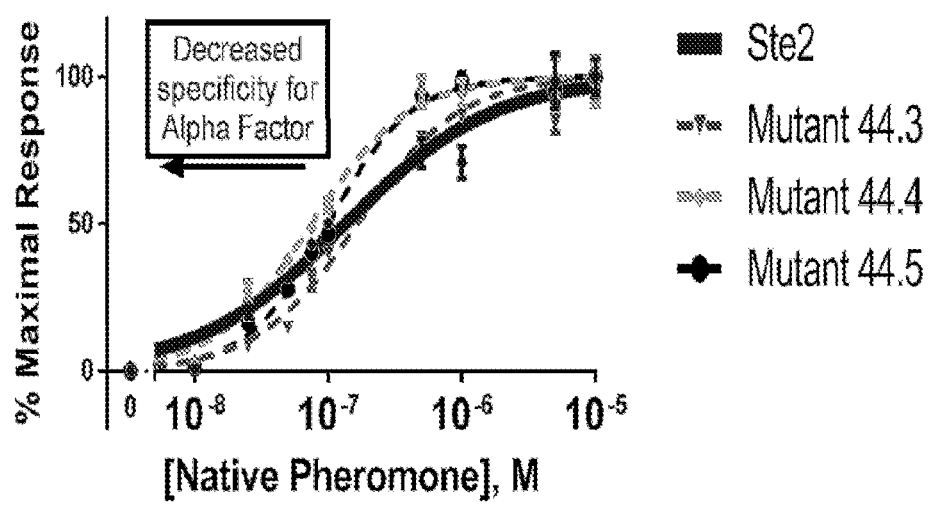
Figure 4:
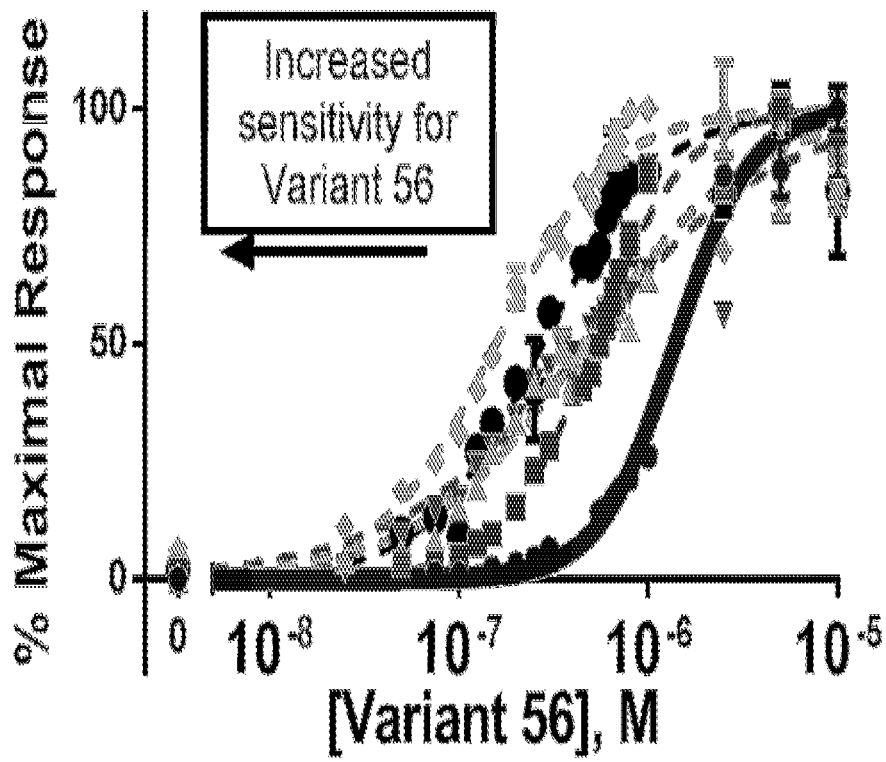
FIG. 4 shows dose response curves for mutants isolated for sensitivity to ligand variant 56 against Variant 56 and the native alpha factor.
Figure 4:
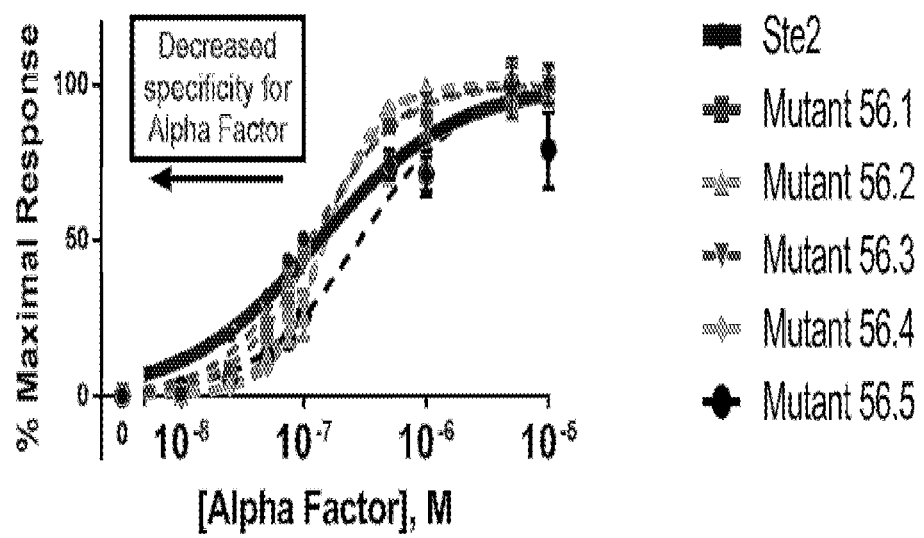

Following the final FACS round, individual clones were selected from the sorted libraries and sequenced using colony PCR. Dose response curves were obtained for individual clones (FIGS. 3 and 4).

Measurements

A half maximal effective concentration (EC50) value, the concentration of ligand that elicited a response halfway between the baseline and maximal responses, for each dose response curve was calculated using GraphPad Prism Software.

Sequencing and Dose Response Curves

Sequencing data from the isolated mutants revealed that mutations in the sixth transmembrane region appeared to increase receptor activity, while mutations found in the earlier transmembrane regions appeared to increase receptor sensitivity for a ligand.

Four of five mutants isolated for activity for ligand Variant 44 had significantly lower EC50 values than Ste2 (FIG. 3A). For ligand Variant 56, all five isolated mutants had significantly lower EC50 values than Ste2 (FIG. 4A). These significantly lower EC50 values imply that the isolated receptors are more sensitive than the native Ste2 receptor is for the specified ligand. Screening the isolated mutants for activity for alpha factor revealed that the mutants maintained some activity for the native alpha factor pheromone (FIGS. 3B and 4B). Even so, two isolated mutants, Mutant 44.1 and Mutant 56.5, showed significantly higher EC50 values than Ste2, implying a decreased specificity for the native alpha factor pheromone.

Figure 7:
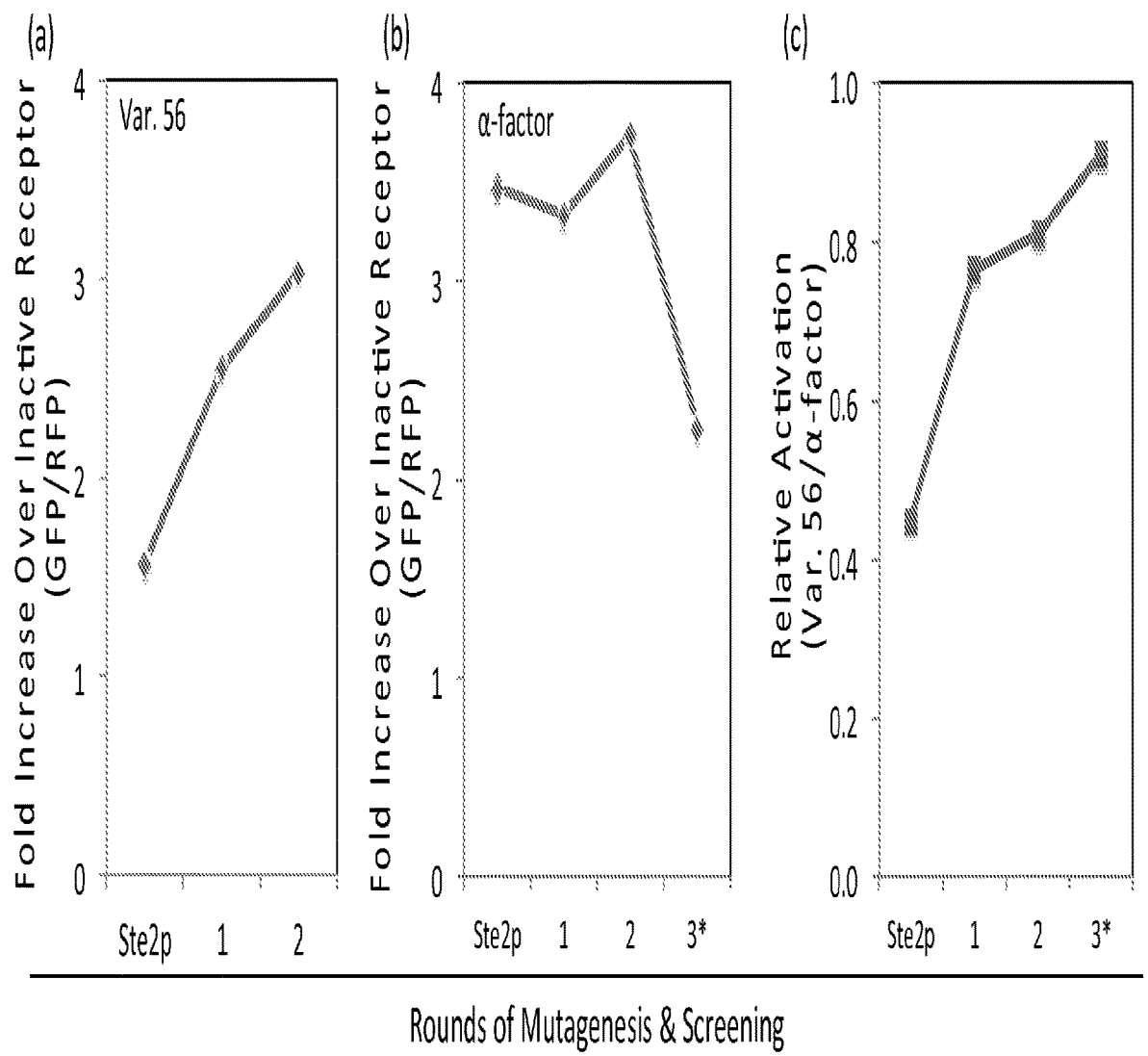
FIG. 7 shows effects of multiple rounds of mutagenesis and screening.
Figure 8:
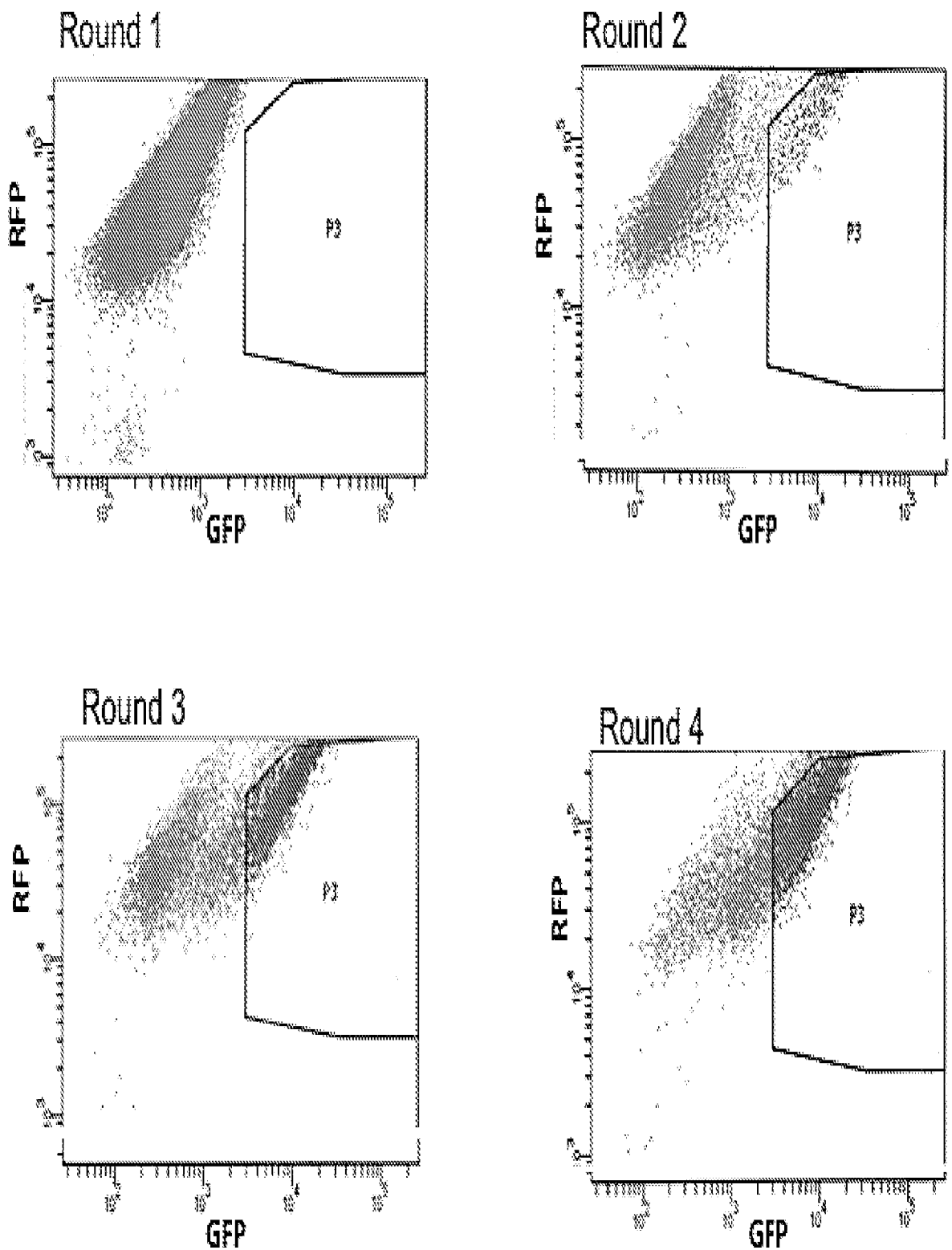
FIG. 8 shows experimental validation that high throughput screen can recover 1 active receptor in $10^6$ inactive receptors. STE2+ yeast cells and STE2− yeast cells were mixed at a $1:10^6$ ratio. α-factor was added to induce the STE2+ cells. The mixture was enriched for high gfp/mKate by FACS. After four rounds of enrichment, a majority of the population was STE2+ (confirmed by colony PCR).

Experiments also demonstrated that sensitivity is increased iteratively (FIG. 7a). A new library was created by re-mutagenizing a mutant receptor that already showed improved sensitivity to variant 56 and screened. The new library displayed increased activity (FIG. 7a). Specificity can be increased with iterative selection and counter-selection (FIG. 7b). Selecting for increased sensitivity to non-native peptides did not also increase sensitivity for α-factor (Fig. b). Round 2 library mutants were also screened for lack of activity for α-factor, confirming the evolution of receptors for specificity against α-factor (FIG. 7c).

Example 2

Yeast Strains and Plasmids

*S. cerevisae* strain MPY578t5 was obtained from Pfizer. The following strains were used for receptor engineering experiments:
1. Strain YJB005 is MPY578t5 with yeast optimized green fluorescent protein (yEGFP) cloned into the FUS1 locus
2. Strain YJB010 is MPY578t5 with red fluorescent protein mKate (also referred to herein as RFP) fused to auxotrophic marker HIS3 cloned into the TRP1 locus
3. Strain YJB013 is MPY578t5 with yEGFP cloned into the FUS1 locus and mKate cloned into the FUS1 locus
4. Strain YJB015 is MPY578t5 with yEGFP cloned into the FUS1 locus, mKate cloned into the FUS1 locus, and contains the pJB036 plasmid
5. Strain YJB017 is MPY578t5 with yEGFP cloned into the FUS1 locus, mKate cloned into the FUS1 locus, and contains the pJB037 plasmid 6. Strain YBA005 is MPY578t5 with yEGFP cloned into the FUS1 locus, mKate-HIS3 cloned into the FUS1 locus, the pJB036 plasmid, and the pFUS1J2 promoter cloned in place of the pFUS1 promoter Plasmid pJB036 (SEQ ID NO:15) is 7067 base pairs long, contains resistance markers for Ampicillin, Uracil3, and ARSH4, and contains yeast Sterile2 (Ste2) receptor between the constitutive GPD promoter and the CYC1 terminator. Plasmids containing yeast libraries are the same as pJB036 but contain mutations in the region coding for the Ste2 gene.

Example 3

Chimera Peptide Approach

Experiments were conducted during development of embodiments herein to use a chimera peptide approach to generate receptors for relevant peptide biomarkers.

Two peptide biomarkers were selected as targets of YBBs development and validation of the system and design strategy. Renal failure and tuberculosis are both global concerns, and would benefit from POC diagnostics.

Renal Failure Biomarker

One in ten American adults experience chronic kidney disease (refs. 13, 14; herein incorporated by reference in their entireties). Cystatin C is a small protein that is cleared from the blood by functional kidneys but accumulates in the blood as a result of kidney malfunction (ref 15; herein incorporated by reference in its entirety). Cystatin C is not detected by a sandwich immunoassay and uses the immunoturbidimetric method instead (ref 16; herein incorporated by reference in its entirety). This method requires a nephelometer to detect the small protein. Because a cystatin C POC diagnostic is not feasible with current technology, urine creatine levels are used instead. Evidence suggests that serum cystatin C levels are a more reliable biomarker and more sensitive to early-onset renal failure compared to urine creatine (ref 17; herein incorporated by reference in its entirety). Therefore a serum cystatin C POC diagnostic would fill an important gap in diagnosing kidney disease. Experiments were conducted during development of embodiments herein to evolve a yeast receptor for recognition of a trypsin fragment of cystatin.

Tuberculosis Biomarker

Tuberculosis continues to be one of the world's deadliest diseases and is the second leading cause of death from an infectious disease worldwide. In 2013, an estimated 9 million people developed clinical TB and 1.5 million died from the disease (ref 18; herein incorporated by reference in its entirety). Globally, 3.5% of new and 20.5% of previously treated cases have multidrug resistant TB and an estimated 9% of patients with MDR TB have extensively drug resistant TB (ref 19; herein incorporated by reference in its entirety). Globally, the success rate for treatment of MDR TB is only 48% making this highly contagious disease even more challenging to manage at the patient and public health level (ref 19; herein incorporated by reference in its entirety). TB treatment requires a drug regiment for six to nine months (ref. 20; herein incorporated by reference in its entirety) with detrimental side effects (ref. 21, 22; herein incorporated by reference in their entireties). During this time, the global standard of care does not include weekly tests to determine the response of TB to the drug. Frequent testing during treatment would solve two problems: (a) allow early detection of drug-resistant strains and (b) allow patients to stop their treatment earlier if the *Mycobacterium* is cleared.

Therefore, a TB POC diagnostic would improve early diagnosis and treatment of TB, as well as complement NAATs for diagnosis.

Recent results have shown that degraded TB proteins can be detected in the urine of TB infected patients by LC-MS (ref. 4; herein incorporated by reference in its entirety). Gramicidin S synthetase 2 (GSS) is a *Mycobacterium tuberculosis* polyketide synthase identified in the LC-MS study. Therefore a urine GSS POC diagnostic could be of specific utility for TB diagnosis.

Yeast Native Receptor System

The yeast pheromone receptor naturally detects a short peptide sequence; the GPCR Ste2p detects the 13 amino acid α-factor, which activates an intracellular mitogen-activated kinase (MAPK) cascade that ultimately activates the promoter FUS1 (ref. 23; herein incorporated by reference in its entirety). There is no crystal structure for Ste2p (as GPCRs are membrane proteins that are notoriously difficult to crystallize (ref. 24; herein incorporated by reference in its entirety)), and only modest information is known about the interactions between α-factor and Ste2p (25). It has been established that the C-terminus of α-factor is responsible for binding to Ste2p, and the N-terminus is responsible for activating signaling. However, rational mutations that redirect Ste2p to detect new ligands are not known. Instead, design methods herein utilize a combinatorial approach that tests millions of random mutations to identify mutations that confer the desired sensitivity to a new peptide.

Directed Evolution of GPCRs

Directed evolution mimics natural evolution, where the 'fitness' is determined by an artificial selection pressure in the laboratory (ref. 26; herein incorporated by reference in its entirety). Directed evolution of GPCRs is a promising area, as natural evolution has produced more than 1,000 different GPCRs that can detect small molecules, peptides, hormones, proteins, and light (ref. 27; herein incorporated by reference in its entirety). Directed evolution is a combinatorial engineering approach that consists of three steps: (a) generating DNA diversity, (b) screening to identify mutations that confer improved properties (e.g., receptor sensitivity/specificity), and (c) characterizing mutants. The process can be iterated by subjecting the isolated mutants to additional mutations to further improve the desired properties. Therefore, via a robust high throughput screen (HTS), a GPCR (e.g., Ste2p) is evolved to detect peptides of interest (POI).

Previous GPCR directed evolution efforts have focused on small molecules rather than peptides. Small molecule ligands cannot interact with many amino acid residues on the receptor, therefore partial binding (a useful evolutionary intermediate) is unlikely. To date, only a limited number of GPCRs have been evolved for small molecules. Examples include: receptors activated solely by synthetic ligand (RASSLs) (ref. 28; herein incorporated by reference in its entirety), designed receptors exclusively activated by designer drugs (DREADDs) (ref. 29: herein incorporated by reference in its entirety), and sugar receptors (ref. 30; herein incorporated by reference in its entirety). Conversely, the 13 amino acid peptide used in the experiments conducted during development of embodiments herein is relatively much larger and can interact with a larger region of the GPCR. With a peptide sequence, it is possible to make intermediate peptides that contain part of the original ligand and part of the target ligand (chimera peptides). Such peptide allow for gradual evolution of the GPCR from the native ligand to the target ligand through a series of intermediate chimeric ligands. A significant of using evolutionary intermediate ligands is the ability to evolve the receptor to detect more divergent substrates. The RASSLs and DREADDS were only able to detect a ligand that varied by a single functional group. By using evolutionary intermediates, the chemical character of the ligand was altered far more (e.g., changing charged groups for hydrophobic groups, truncating the ligand, etc.).

Results

Experiments conducted during development of embodiments herein demonstrate successful development of a high throughput screen (HTS) for GPCR activation that uses fluorescence activated cell sorting (FACS). Receptor activation was coupled to green fluorescent protein (GFP) expression by cloning GFP downstream of the Ste2p-activated FUS1 promoter. Therefore a receptor mutant that is successfully activated by the POI will result in the cell fluorescing green. The discriminating power of the screen is improved by including an internal control, constitutive expression of mKate (a red fluorescent protein). Red fluorescence corresponds to cell size, and allows us to normalize the GFP measurement for more accurate sorting. This screen can select one activated receptor in one million inactive receptors. The initial HTS has false positive (FP) rates of 20% and false negative (FN) rates of 10%. The FP and FN rate is overcome by doing multiple rounds of enrichment. In four rounds of enrichment, a population of cells is isolated that originally was 1 in $10^6$. This screen has superior discriminating power compared to previous growth-based selections (ref. 29; herein incorporated by reference in its entirety).

Engineered Receptors can Specifically Detect Many Peptide Sequences Including Biomarker Chimeras.

Experiments conducted during development of embodiments herein have demonstrated the ability to retarget Ste2p to detect several new ligands using directed evolution. Experiments have demonstrated: (a) engineering receptors that can detect single amino acid variants of α-factor that Ste2p cannot, (b) continuous improvement of receptor sensitivity by multiple directed evolution cycles, and (c) increased specificity of receptors by selecting for receptors that are 'off' in the presence of the non-target ligand. Experiments conducted during development of embodiments herein have also demonstrated that detection of peptides in serum.

Figure 9:
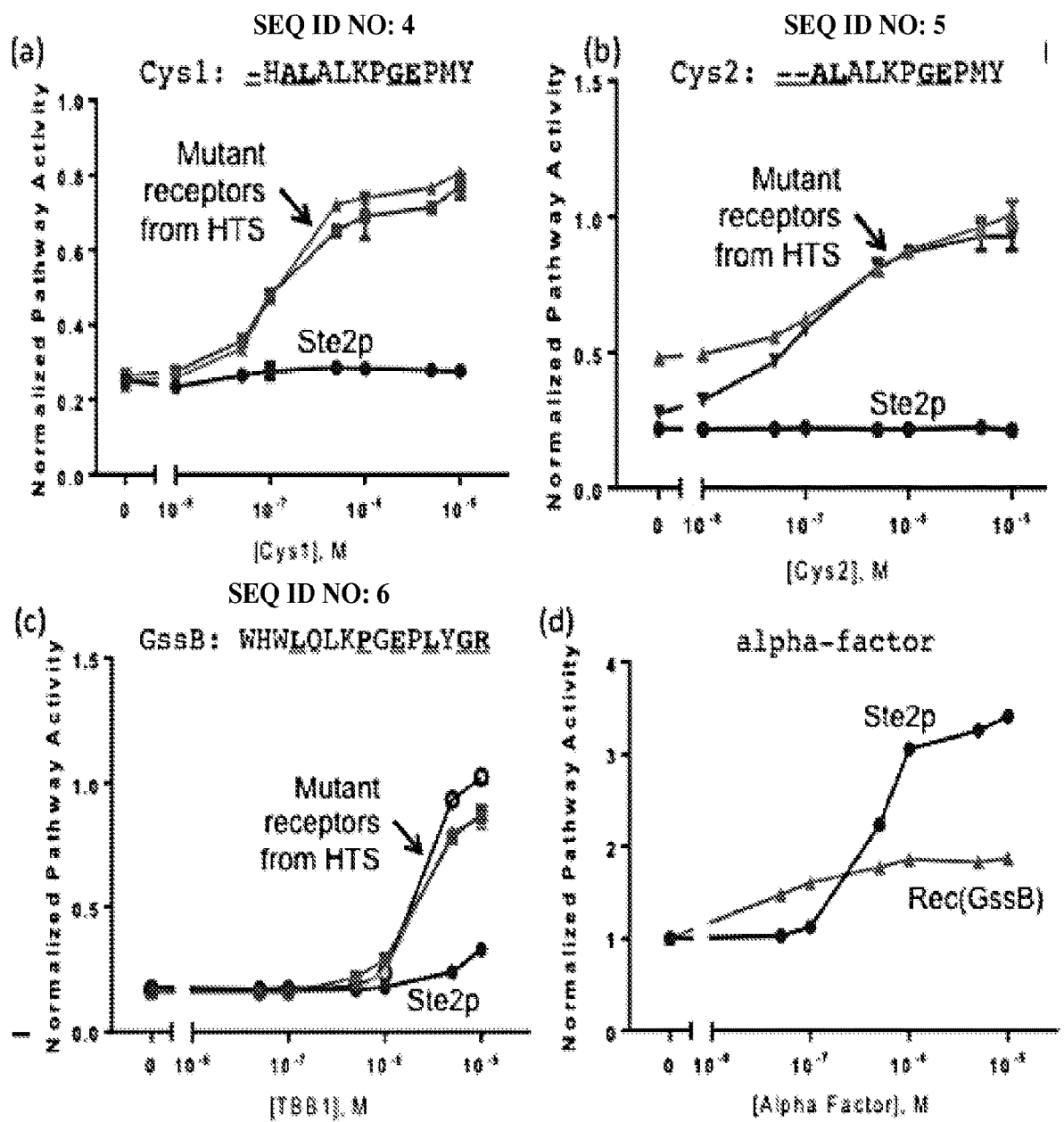
FIG. 9 shows that receptors for biomarker chimeras have improved dose-response curves. (a) Mutant receptors have a lower EC50 to Cys1 than $Rec_{Ste2p}$. (b) Mutant receptors (derived from $Rec_{Cys1}$ mutagenesis) have lower EC50 to Cys2 than $Rec_{Ste2p}$. (c) Mutant receptors have a lower EC50 to GssB than $Rec_{Ste2p}$. (d) Mutant receptor $Rec_{GssB}$ from (c) no longer responds to α-factor. Bold & underlined sequences are common with the target peptide.

Experiments conducted during development of embodiments herein have demonstrated generation of receptors that recognize partial sequences of cystatin and GSS. Initial attempts to evolve directly for the cystatin/GSS peptides were unsuccessful. To take smaller evolutionary steps, chimera peptides were designed that were more similar to α-factor. Receptors were evolved to recognize peptide that contain several changes in the peptide sequence (FIG. 9a-c). The evolved receptors do not respond to the native ligand, demonstrating specificity improvements, see FIG. 9D).

Example 4

Further Evolution of Receptors

A series of chimera peptides have been designed based on the available structural information (ref. 31; herein incorporated by reference in its entirety) for use in the directed evolution of Ste2p (Table 1).

TABLE 1

Ligand chimeras with increasing target sequence

| | Cystatin chimeras | | CSS chimeras | |
|---|---|---|---|---|
| SEQ ID NO: 1 α-factor | WHWLQLKPGQPMY | α-factor | WHWLQLKPGQPMY-- | SEQ ID NO: 1 |
| SEQ ID NO: 4 Cys1 | -HALALKPGEPMY | GssB# | WHWLQLKPGEPLYGR | SEQ ID NO: 6 |
| SEQ ID NO: 5 Cys2 | --ALALKPGEPMY | GssS## | LHLLALKPGQPMY-- | SEQ ID NO: 10 |
| SEQ ID NO: 7 Cys3 | --ALDFKPGEPMY | Gss1 | LRLLALKPGQPLYGR | SEQ ID NO: 11 |
| SEQ ID NO: 8 Cys4 | --ALDLAVGEPMY | Gss2 | LHLLAGQPGESLYGR | SEQ ID NO: 12 |
| SEQ ID NO: 9 Cys5* | --ALDFAVGEYNK | Gss3** | LLLLAGQPEESLAGR | SEQ ID NO: 13 |

*Cystatin
**GSS peptide
C-term binding region is GSS
N-term signaling region is GSS Receptors have been successfully evolved for some chimeras. Two steps have been completed for cystatin (evolving for Cys1 and then using that receptor as a parent to evolve for Cys2) and one step for GSS.

For cystatin, a step-wise chimera strategy has been used to develop a receptor that detects the final cystatin sequence.

For GSS, a structure-driven approach is pursued. Mutations that enhance the response to GssB have been shown to also enhance response to Gss1. Mutant receptors responsive to Gss1 may be subjected to additional rounds of directed evolution to find mutants that allow for response to Gss2 and Gss3.

Example 5

Sensitivity Enhancement

Figure 11:
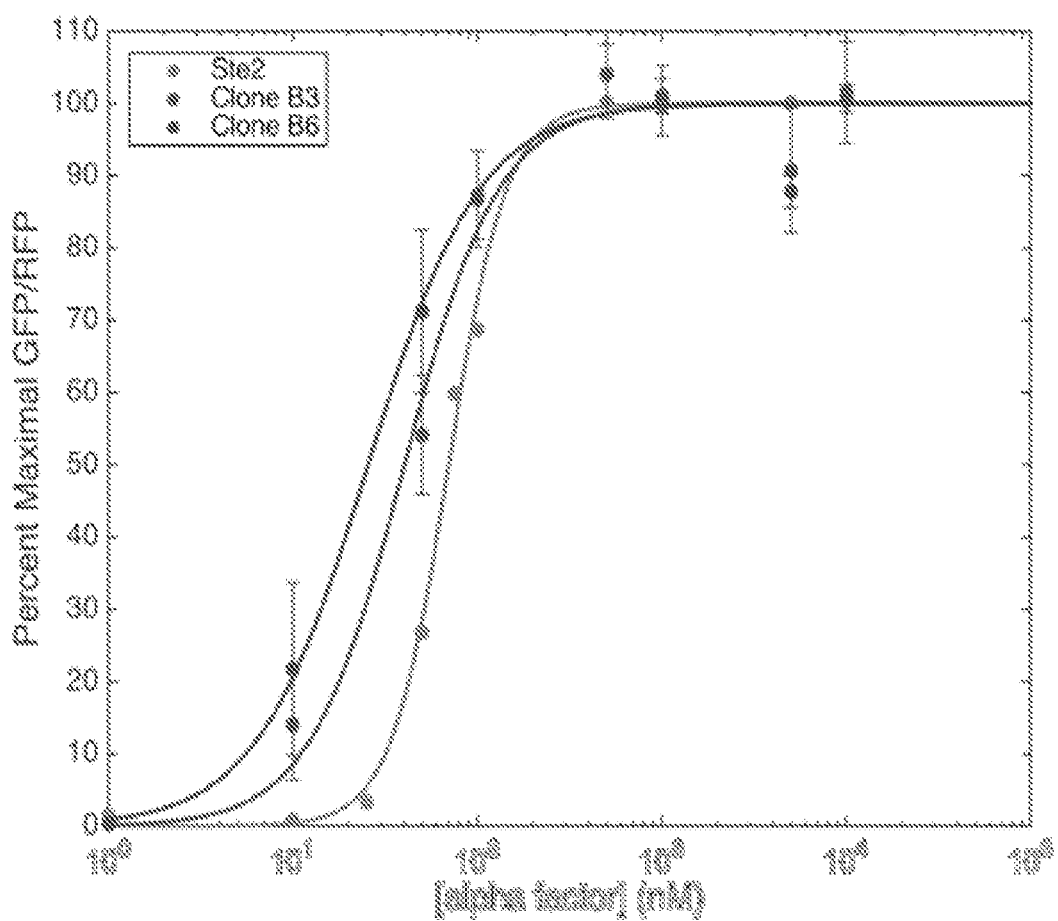
FIG. 11 shows a dose response curve demonstrating sensitivity enhancement of evolved receptors.

Experiments were conducted during development of embodiments of the present invention that demonstrate evolution of receptors that respond to α-factor at concentrations lower than the wild type/Ste2p receptor (SEE FIG. 11).

Example 6

Specificity Enhancement

Figure 12:
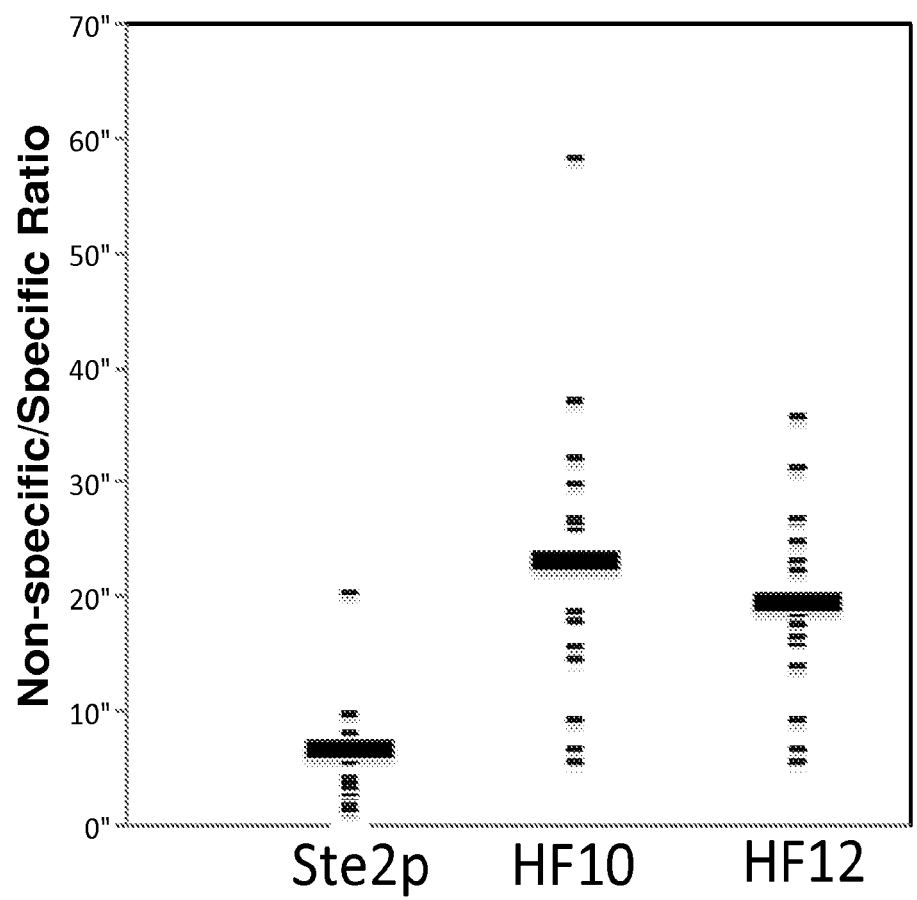
FIG. 12 shows enhanced discrimination against non-target peptides for evolved receptors.

Experiments were conducted during development of embodiments of the present invention that demonstrate evolution of a receptor with enhanced discrimination against non-target peptides that differ from the target peptide by as few as 1 amino acid (FIG. 12).

Example 7

Orthogonality

Figure 13A:
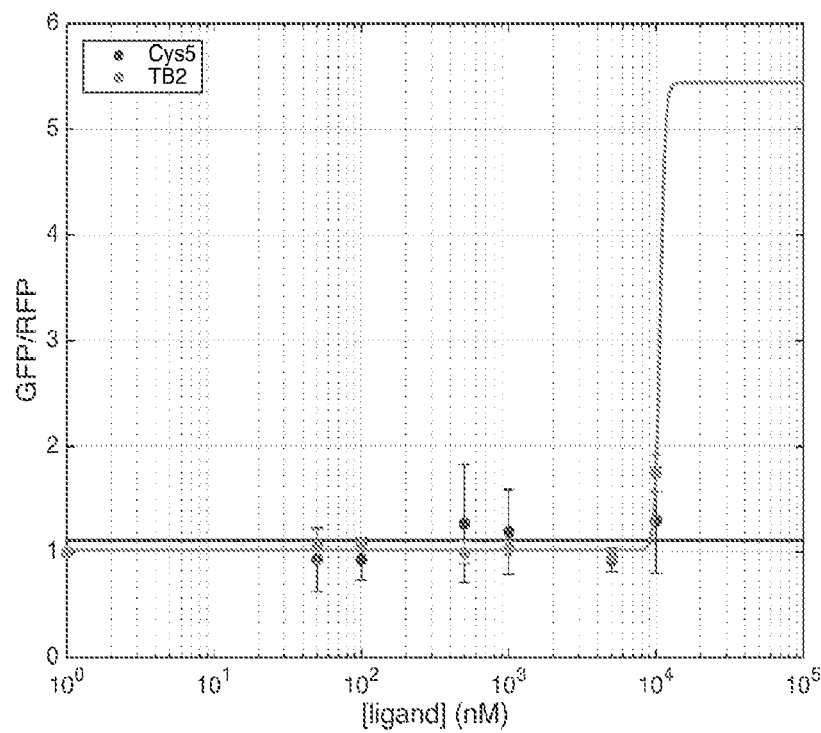
FIGS. 13A and 13B show dose response curves in response to Cys5 and TB2 for (A) tuberculosis receptor and (B) cystatin receptor.
Figure 13B:
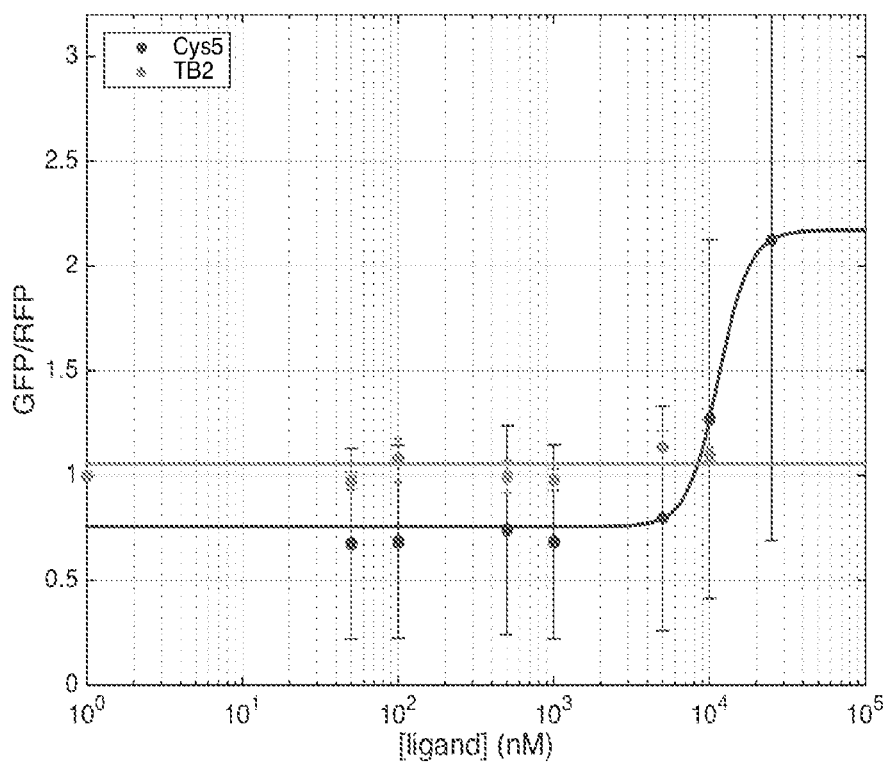
Figure 14A:
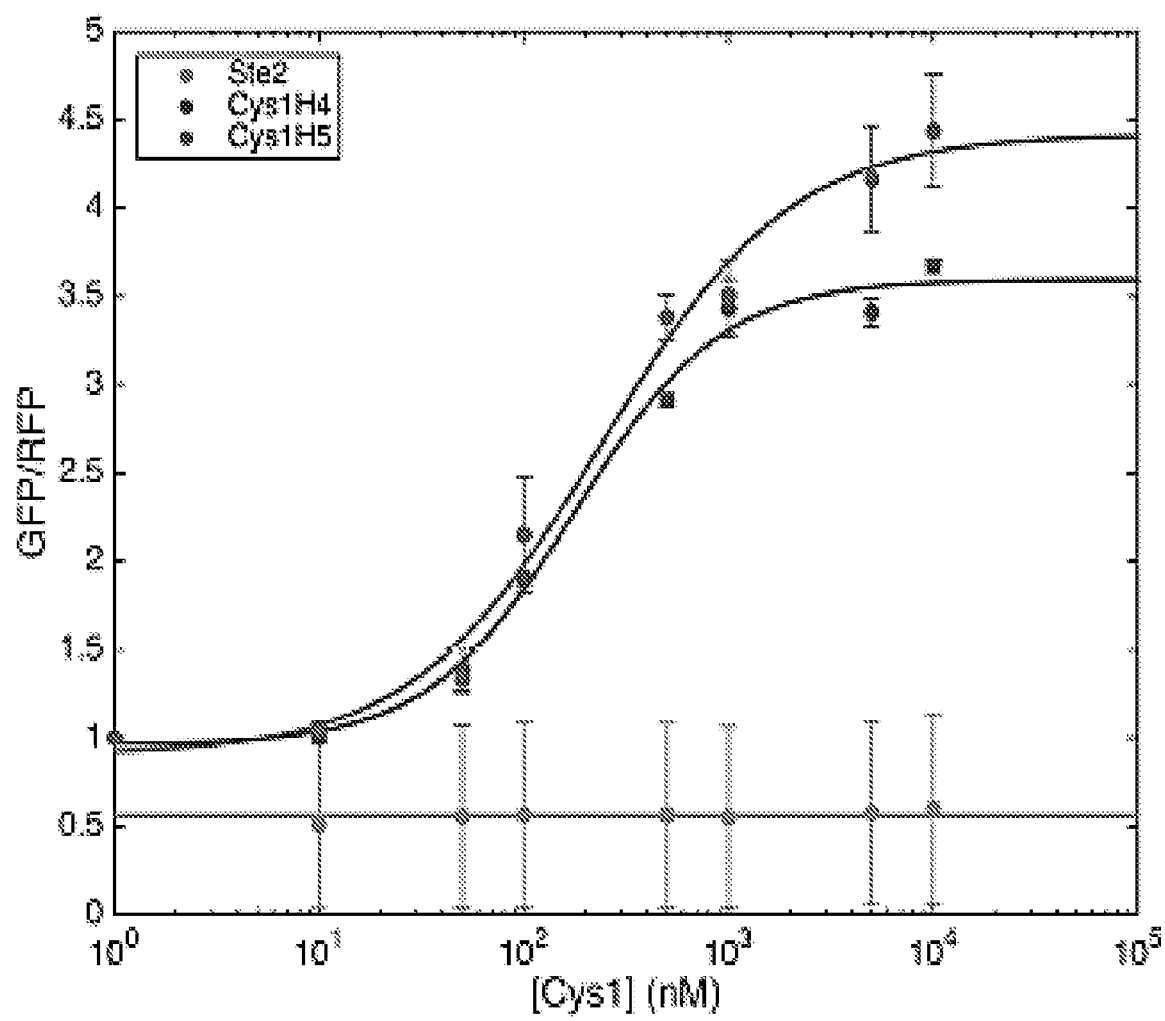
FIGS. 14A-14D show dose response curves of YBBs expressing evolved receptor linked to expression of GFP and a control RFP responding to cystatin peptides (A) Cys1, (B) Cys4, and (C) Cys5, and (D) a plot of evolution trajectory indicating increased specificity and sensitivity.
Figure 14B:
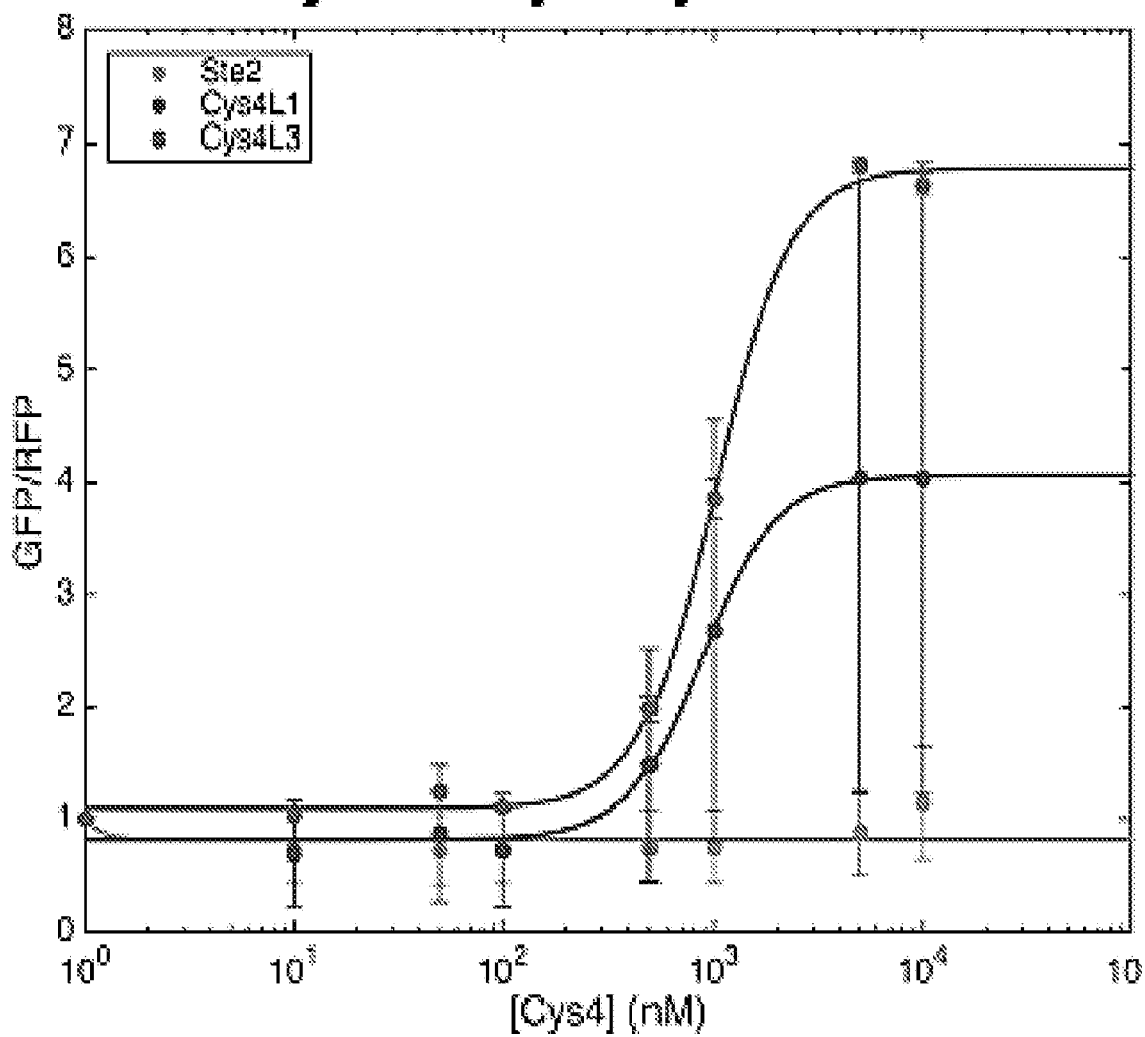
Figure 14C:
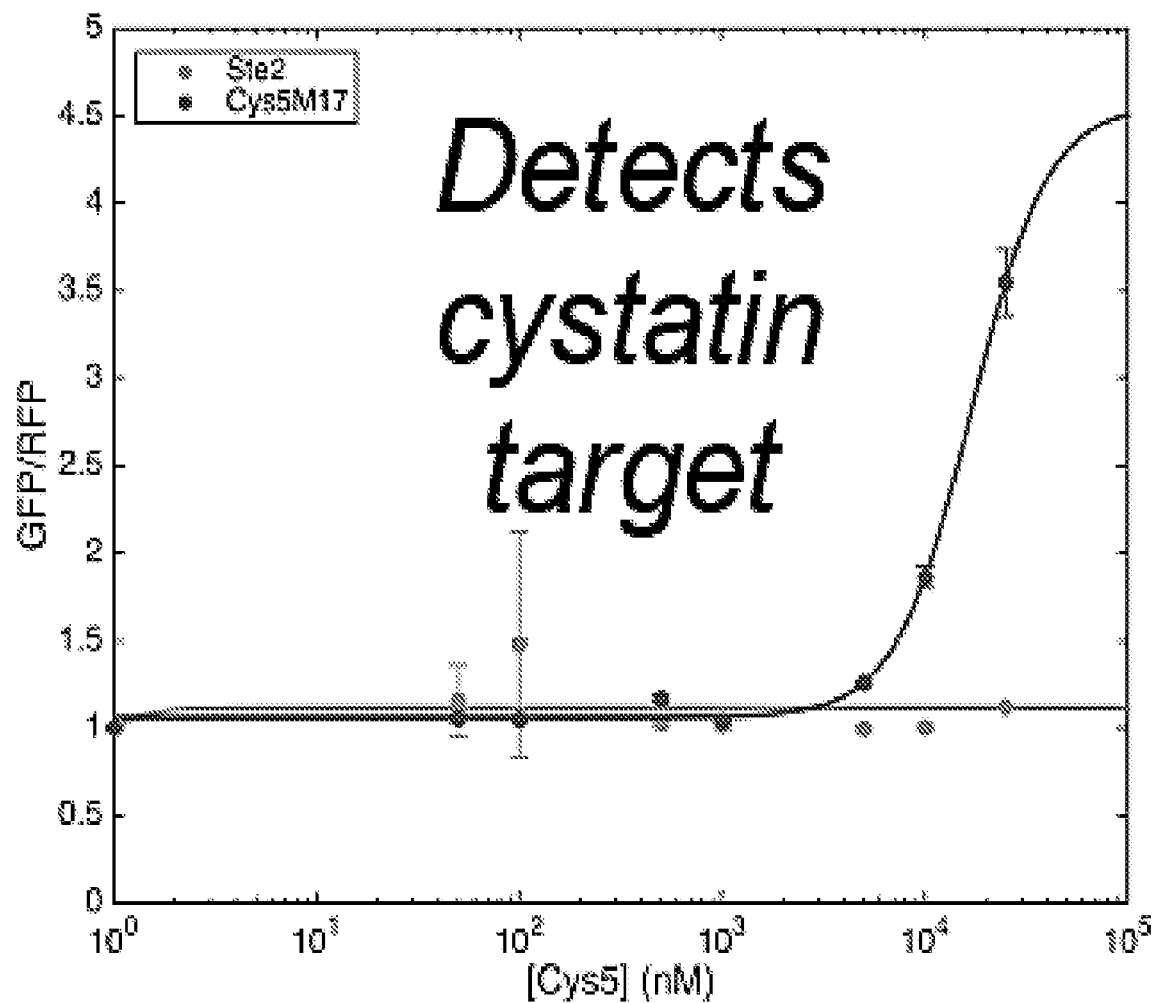
Figure 14D:
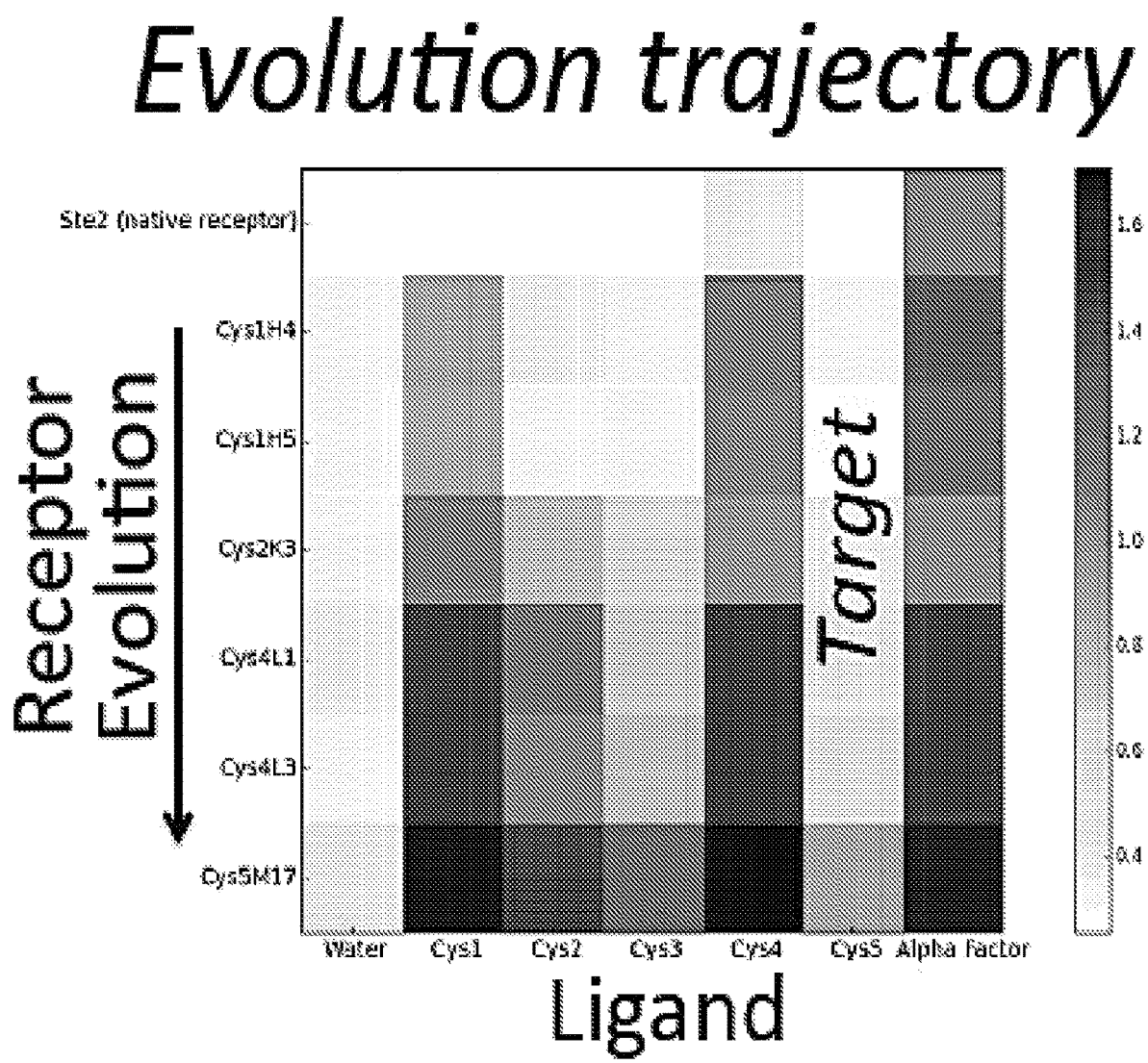

Experiments were conducted during development of embodiments herein that demonstrate orthogonality of the evolved receptors (FIG. 13). The evolved Tuberculosis receptor responds to GSS fragment (TB2 peptide), but Ste2p receptor does not (FIG. 13A). Similarly, the evolved cystatin receptor rises in response to Cys5 (native cystatin) but not TB2 (FIG. 13B).

Example 8

Renal Failure Diagnostic

Receptor mutants (evolved from Ste2p) were selected that respond to the intermediate and final (Cys5) cystatin peptides. Dose response curves show the mutant receptor responds to the cognizant peptide, but Ste2p does not (FIG. 14A-C). The evolutionary trajectory (FIG. 14D) demonstrates a broadening of specificity as well as increased sensitivity.

Example 9

Exemplary Recognition Elements

Table 2 contains mutations relative the SEQ ID NO: 1 contained in exemplary recognition elements generated by the methods described herein.

TABLE 2

| Receptor | Amino Acid Mutations from Ste2 |
|---|---|
| Cys1H4 | M54I |
| Cys1H5 | M54I, C59S |
| Cys2K3 | M54I, N158Y, M218T, K225T, S356T |
| Cys4L3 | Y26F, M54I, R74K, N158F, T167R, M218T, K225T, Y320X |
| Cys5M17 | Y26F, M54I, R74K, N158I, T167R, M218T, K225T, Y320X |

REFERENCES

The following references, some of which are cited above by number, are herein incorporated by reference in their entireties.

1. Aluise C D, Sowell R A, Butterfield D A. Peptides and proteins in plasma and cerebrospinal fluid as biomarkers for the prediction, diagnosis, and monitoring of therapeutic efficacy of Alzheimer's disease. Biochim Biophys Acta. 2008; 1782(10):549-58.
2. Petricoin E F, Belluco C, Araujo R P, Liotta L A. The blood peptidome: a higher dimension of information content for cancer biomarker discovery. Nature reviews Cancer. 2006; 6(12):961-7.
3. Stalmach A, Johnsson H, McInnes I B, Husi H, Klein J, Dakna M, Mullen W, Mischak H, Porter D. Identification of urinary peptide biomarkers associated with rheumatoid arthritis. PloS one. 2014; 9(8):e104625.
4. Young B L, Mlamla Z, Gqamana P P, Smit S, Roberts T, Peter J, Theron G, Govender U, Dheda K, Blackburn J. The identification of tuberculosis biomarkers in human urine samples. The European respiratory journal. 2014.
5. McDonnell B, Hearty S, Leonard P, O'Kennedy R. Cardiac biomarkers and the case for point-of-care testing. Clinical biochemistry. 2009; 42(7-8):549-61.
6. Tucker J D, Bien C H, Peeling R W. Point-of-care testing for sexually transmitted infections: recent advances and implications for disease control. Current opinion in infectious diseases. 2013; 26(1):73-9
7. Weigl B H, Neogi T, McGuire H. Point-of-Care Diagnostics in Low-Resource Settings and Their Impact on Care in the Age of the Noncommunicable and Chronic Disease Epidemic. Journal of laboratory automation. 2013; 19(3): 248-57.
8. Chepurny O G, Holz G G. A novel cyclic adenosine monophosphate responsive luciferase reporter incorporating a nonpalindromic cyclic adenosine monophosphate response element provides optimal performance for use in G protein coupled receptor drug discovery efforts. Journal of biomolecular screening. 2007; 12(5):740-6.
9. McCusker E C, Bane S E, O'Malley M A, Robinson A S. Heterologous GPCR expression: a bottleneck to obtaining crystal structures. Biotechnology progress. 2007; 23(3): 540-7.
10. Shevchenko A, Wilm M, Mann M. Peptide sequencing by mass spectrometry for homology searches and cloning of genes. Journal of protein chemistry. 1997; 16(5):481-90.
11. LifeTechnologies. TrypLE™ Express Enzyme (1×), no phenol red accessed 2014. tools.lifetechnologies.com/content/sfs/manuals/tryplE_man.pdf.
12. Keppler-Ross S, Noffz C, Dean N. A new purple fluorescent color marker for genetic studies in *Saccharomyces cerevisiae* and *Candida albicans*. Genetics. 2008; 179(1):705-10.
13. Coresh J, Selvin E, Stevens L A, Manzi J, Kusek J W, Eggers P, Van Lente F, Levey A S. Prevalence of chronic kidney disease in the United States. Jama. 2007; 298(17): 2038-47.
14. Center for Disease Control and Prevention. Chronic Kidney Disease (CKD) Surveillance Project: Prevalence of CKD Stages 2015 [cited 2015 Feb. 16]. nccd.cdc.gov/CKD/detail.aspx?Qnum=Q8.
15. Randers E, Erlandsen E J, Pedersen O L, Hasling C, Danielsen H. Serum cystatin C as an endogenous parameter of the renal function in patients with normal to moderately impaired kidney function. Clinical nephrology. 2000; 54(3):203-9.
16. Lewis A V, James T J, McGuire J B, Taylor R P. Improved immunoturbidimetric assay for cystatin C. Annals of clinical biochemistry. 2001; 38(Pt 2):111-4.
17. Dharnidharka V R, Kwon C, Stevens G. Serum cystatin C is superior to serum creatinine as a marker of kidney function: a meta-analysis. American journal of kidney diseases: the official journal of the National Kidney Foundation. 2002; 40(2):221-6.
18. Center for Disease Control and Prevention. Tuberculosis: Data & Statistics 2015 [cited 2015 Feb. 16]. cdc.gov/tb/statistics/default.htm.
19. World Health Organization. Global Tuberculosis Report (2014). France: World Health Organization, 2014.
20. Center for Disease Control and Prevention. Tuberculosis: Treatment 2015 [cited 2015 Feb. 16]. cdc.gov/tb/topichreatment/default.htm.
21. Schaberg T, Rebhan K, Lode H. Risk factors for side-effects of isoniazid, rifampin and pyrazinamide in patients 22. Tekle B, Mariam D H, Ali A. Defaulting from DOTS and its determinants in three districts of Arsi Zone in Ethiopia. The international journal of tuberculosis and lung disease: the official journal of the International Union against Tuberculosis and Lung Disease. 2002; 6(7):573-9.
23. Herskowitz I. MAP kinase pathways in yeast: for mating and more. Cell. 1995; 80(2):187-97.
24. Kobilka B, Schertler G F. New G-protein-coupled receptor crystal structures: insights and limitations. Trends in pharmacological sciences. 2008; 29(2):79-83.
25. Naider F, Becker J M. The alpha-factor mating pheromone of Saccharomyces cerevisiae: a model for studying the interaction of peptide hormones and G protein-coupled receptors. Peptides. 2004; 25(9):1441-63.
26. Romero P A, Arnold F H. Exploring protein fitness landscapes by directed evolution. Nature reviews Molecular cell biology. 2009; 10(12):866-76. doi: 10.1038/nrm2805.
27. Rosenbaum D M, Rasmussen S G, Kobilka B K. The structure and function of G-protein-coupled receptors. Nature. 2009; 459(7245):356-63.
28. Coward P, Wada H G, Falk M S, Chan S D, Meng F, Akil H, Conklin B R. Controlling signaling with a specifically designed Gi-coupled receptor. Proceedings of the National Academy of Sciences of the United States of America. 1998; 95(1):352-7.
29. Armbruster B N, Li X, Pausch M H, Herlitze S, Roth B L. Evolving the lock to fit the key to create a family of G protein-coupled receptors potently activated by an inert ligand. Proceedings of the National Academy of Sciences of the United States of America. 2007; 104(12):5163-8.
30. Ault A D, Broach J R. Creation of GPCR-based chemical sensors by directed evolution in yeast. Protein engineering, design & selection: PEDS. 2006; 19(1):1-8.
31. Abel M G, Lee B K, Naider F, Becker J M. Mutations affecting ligand specificity of the G-protein-coupled receptor for the Saccharomyces cerevisiae tridecapeptide pheromone. Biochim Biophys Acta. 1998; 1448(1):12-26.
32. Lee Biosolutions. 2015. leebio.com/category/human-biological-fluids.

The invention claimed is:

1. A yeast-based biosensor comprising a yeast cell expressing:
   (a) a recognition element that is a modified version of a native yeast cell-surface receptor, wherein the recognition element binds to a peptide analyte that is not a natural ligand for the native yeast cell-surface receptor, and wherein the peptide analyte comprises less than 50% sequence identity with the natural ligand for the native yeast cell-surface receptor; and
   (b) a reporter, expression of which is linked to binding of the recognition element to the peptide analyte.

2. The yeast-based biosensor of claim 1, wherein the yeast cell is an engineered yeast cell.

3. The yeast-based biosensor of claim 1, wherein the recognition element is surface-exposed.

4. The yeast-based biosensor of claim 3, wherein the surface-exposed recognition element is a modified yeast G protein-coupled receptor (GPCR).

5. The yeast-based biosensor of claim 4, wherein the modified GPCR maintains the signal transduction functionality of a native yeast GPCR with modified analyte recognition functionality.

6. The yeast-based biosensor of claim 5, wherein the modified GPCR induces a G-protein signal transduction cascade upon binding the peptide analyte.

7. The yeast-based biosensor of claim 1, wherein the recognition element is a modified Ste2p receptor.

8. The yeast-based biosensor of claim 7, wherein the recognition element binds a peptide fragment of gramicidin S synthetase 2 or cystatin C.

9. The yeast-based biosensor of claim 8, wherein the recognition element does not bind native alpha factor.

10. The yeast-based biosensor of claim 1, wherein the reporter comprises:
 (i) a promoter, and
 (ii) a detectable element under expression control of said promoter.

11. The yeast-based biosensor of claim 10, wherein expression from said promoter is altered by signal transduction from said surface-exposed recognition element.

12. The yeast-based biosensor of claim 10, wherein expression from said promoter is enhanced by signal transduction from said surface-exposed recognition element.

13. The yeast-based biosensor of claim 10, wherein the detectable element is a luciferase, fluorescent protein, or metabolite.

14. The yeast-based biosensor of claim 1, further comprising a control reporter that produces a detectable signal independent of binding of the peptide analyte and the recognition element.

15. The yeast-based biosensor of claim 1, further comprising: (c) a second surface-exposed recognition element that binds a second non-native peptide analyte; and (d) a second reporter that produces a detectable signal in response to binding of the second peptide analyte and the second recognition element; wherein the first and second reporters produce distinguishable detectable signals.

16. A method of detecting a peptide analyte in a sample, comprising:
 (a) contacting a sample with the composition of claim 1; and
 (b) detecting the detectable signal from said reporter.

17. The method of claim 16, further comprising comparing the detectable signal from said reporter to a control signal.

18. The method of claim 17, wherein the control signal is the detectable signal from said reporter before contacting the sample with the artificial cellular entity.

19. The method of claim 16, wherein said sample is an environment, biological, security, or forensic sample.

20. The method of claim 19, wherein said sample is a biological sample selected from blood, a blood product, urine, and saliva.

* * * * *